(12) United States Patent
Shekel et al.

(10) Patent No.: US 7,351,349 B2
(45) Date of Patent: Apr. 1, 2008

(54) METHOD AND APPARATUS FOR REAL-TIME DYNAMIC CHEMICAL ANALYSIS

(75) Inventors: Yehuda Shekel, Jerusalem (IL); Ira M Hartman, Hashmonaim (IL); George A Thompson, Santa Clara, CA (US)

(73) Assignee: ECI Technology, Inc., Totowa, NJ (US)

( * ) Notice: Subject to any disclaimer, the term of this patent is extended or adjusted under 35 U.S.C. 154(b) by 136 days.

(21) Appl. No.: 10/807,537

(22) Filed: Mar. 23, 2004

(65) Prior Publication Data

US 2005/0028932 A1 Feb. 10, 2005

Related U.S. Application Data

(63) Continuation of application No. PCT/IL02/00779, filed on Sep. 19, 2002.

(30) Foreign Application Priority Data

Sep. 25, 2001 (IL) .................................... 145649

(51) Int. Cl.
*B44C 1/22* (2006.01)
*C03C 15/00* (2006.01)
*C03C 25/68* (2006.01)
*C23F 1/00* (2006.01)
(52) U.S. Cl. .................................................. 216/85
(58) Field of Classification Search ............... 216/81, 216/85, 84, 94; 451/8, 1, 5; 134/18
See application file for complete search history.

(56) References Cited

U.S. PATENT DOCUMENTS 4,060,097 A 11/1977 Oxford (Continued)

FOREIGN PATENT DOCUMENTS

JP     63009124 A  *  1/1988

(Continued)

OTHER PUBLICATIONS

De Keersmacker, R., Dielectric Breakdown in Thermally Growing Oxide Layer, Chapter 7, Katolieke Universitett Leuven, Belgium 1993.

(Continued)

*Primary Examiner*—Roberts Culbert

(57) ABSTRACT

Methods and apparatus for real-time dynamic analysis of a chemical etching process are provided. The apparatus comprises an optical element (36) operative to pass a beam of electromagnetic radiation at least at two points in time through a liquid phase (42) comprising at least one chemical component and including an etchant, wherein the etchant is operative to etch a solid. A detector (60) is operative to perform an ex-situ non-contact scanning detection of the electromagnetic radiation subsequent to passing through the liquid phase in a near infra-red range (700-2500 nm) at the at least at two points in time so as to detect a change in an optical property of at least one of the at least one chemical component and the etchant. The apparatus further comprises a processor (64) operative to activate an algorithm so as to compare the change in the optical property of the at least of the at least one chemical component and the etchant received from the detector so as to provide data concerning a change in concentration of the etchant; and further configured to perform a chemometric manipulation of the data so as to provide a rate of etching of the solid.

17 Claims, 19 Drawing Sheets

U.S. PATENT DOCUMENTS

| | | | |
|---|---|---|---|
| 4,454,001 | A | 6/1984 | Sternheim et al. |
| 4,710,261 | A | 12/1987 | Dennis |
| 5,097,130 | A | 3/1992 | Koashi et al. |
| 5,337,144 | A | 8/1994 | Strul et al. |
| 5,376,214 | A | 12/1994 | Iwasaki et al. |
| 5,392,124 | A | 2/1995 | Barbee et al. |
| 5,450,205 | A | 9/1995 | Sawin et al. |
| 5,500,073 | A | 3/1996 | Barbee et al. |
| 5,516,399 | A | 5/1996 | Balconi-Lamica et al. |
| 5,573,623 | A | 11/1996 | Barbee et al. |
| 5,573,624 | A | 11/1996 | Barbee et al. |
| 5,582,746 | A | 12/1996 | Barbee et al. |
| 5,694,207 | A | 12/1997 | Huang et al. |
| 5,788,801 | A | 8/1998 | Barbee et al. |
| 5,830,375 | A | 11/1998 | Huang et al. |
| 5,893,046 | A | 4/1999 | Wu et al. |
| 5,938,885 | A | 8/1999 | Huang et al. |
| 6,013,165 | A | 1/2000 | Wiktorowicz et al. |
| 6,203,659 | B1 | 3/2001 | Shen et al. |
| 6,270,986 | B1 | 8/2001 | Wong |

FOREIGN PATENT DOCUMENTS

| | | | |
|---|---|---|---|
| JP | 63307334 A | * | 12/1988 |

OTHER PUBLICATIONS

Judge, John S., "A Study of the Dissolution of SiO2 in Acidic Fluoride Solutions", J. Electrochem. Soc., Nov. 1971, pp. 1772-1775.

Moore, Walter J., "Physical Chemistry", 4th Edition, Longmans, 1963.

Carpio, Ronald, et al., "Concentration Control of SC-1 Megasonic Processing Baths", Electrochemical Society Proceedings (1994), vol. 4, Section III, pp. 253-266.

Burns, Donald, et al., ed., "Handbook of Near-Infrared Analysis", Marcel Dekker Inc., 1992.

Kashkoush, Ismail, et al., "In-Situ Chemical Concentration Control for Wafer Wet Cleaning", Mat. Res. Soc. Symp. Proc. (1997), vol. 477, p. 311-316.

Fischer, Wolfgag B., et al., "Corrections to the Baseline Distortions in the OH-Stretch Region of Aqueous Solutions", Appl. Spec. 1994, vol. 48 (1), pp. 107-112.

Thompson, Christopher J., et al., "Quantification of Hydrofluoric Acid Species by Chemical-Modeling Regression of Near-Infrared Spectra", Anal. Chem. 1997, vol. 69, pp. 25-35.

* cited by examiner

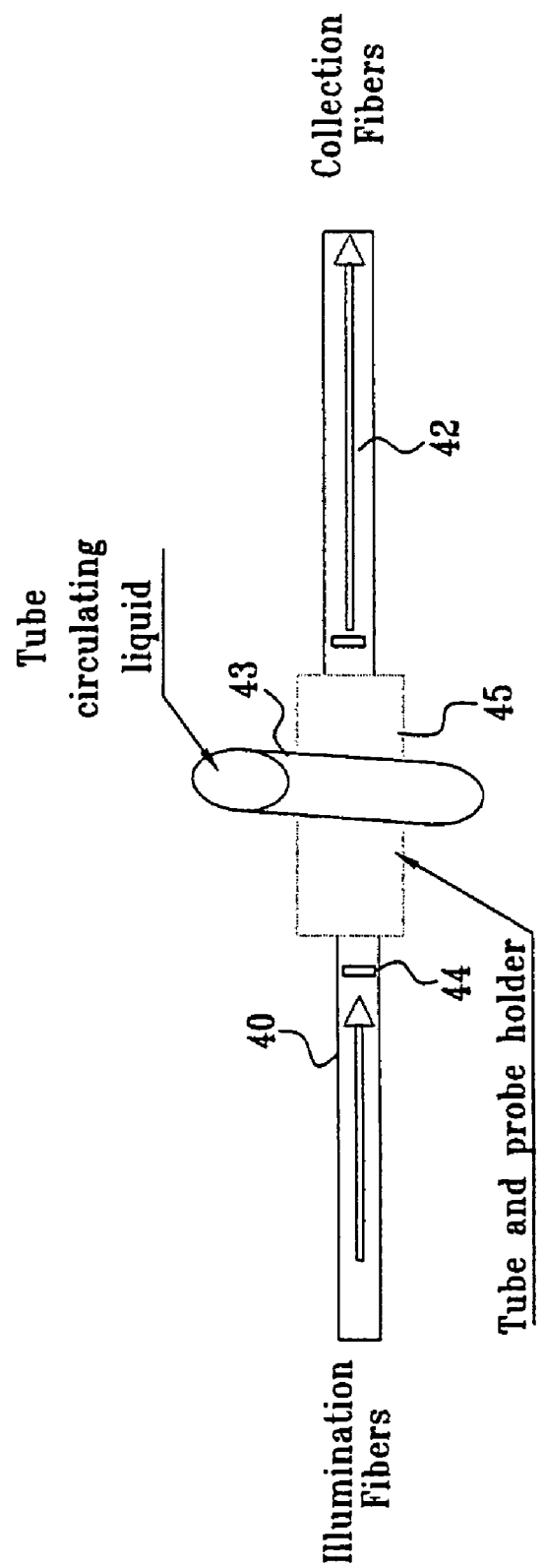

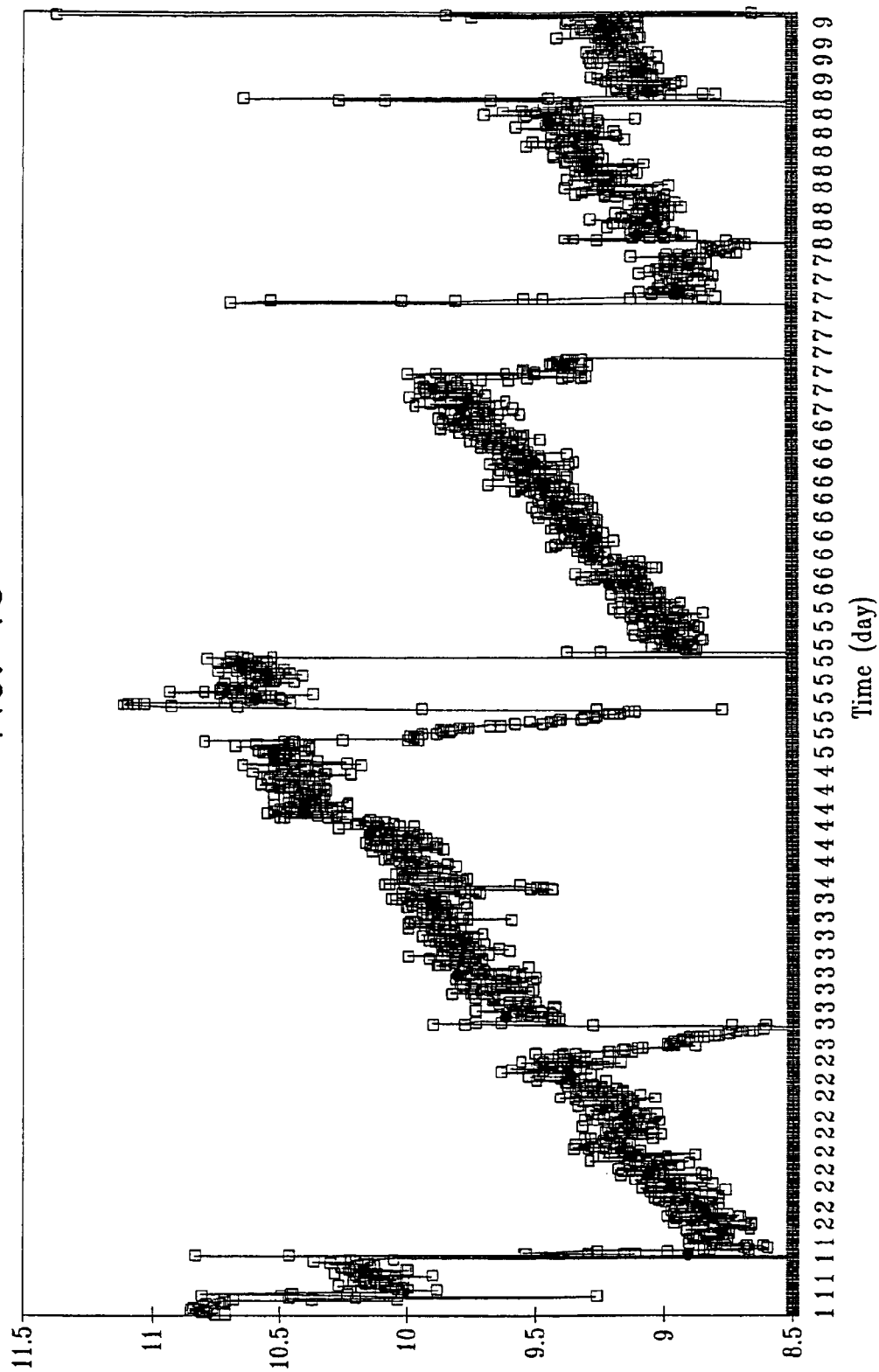

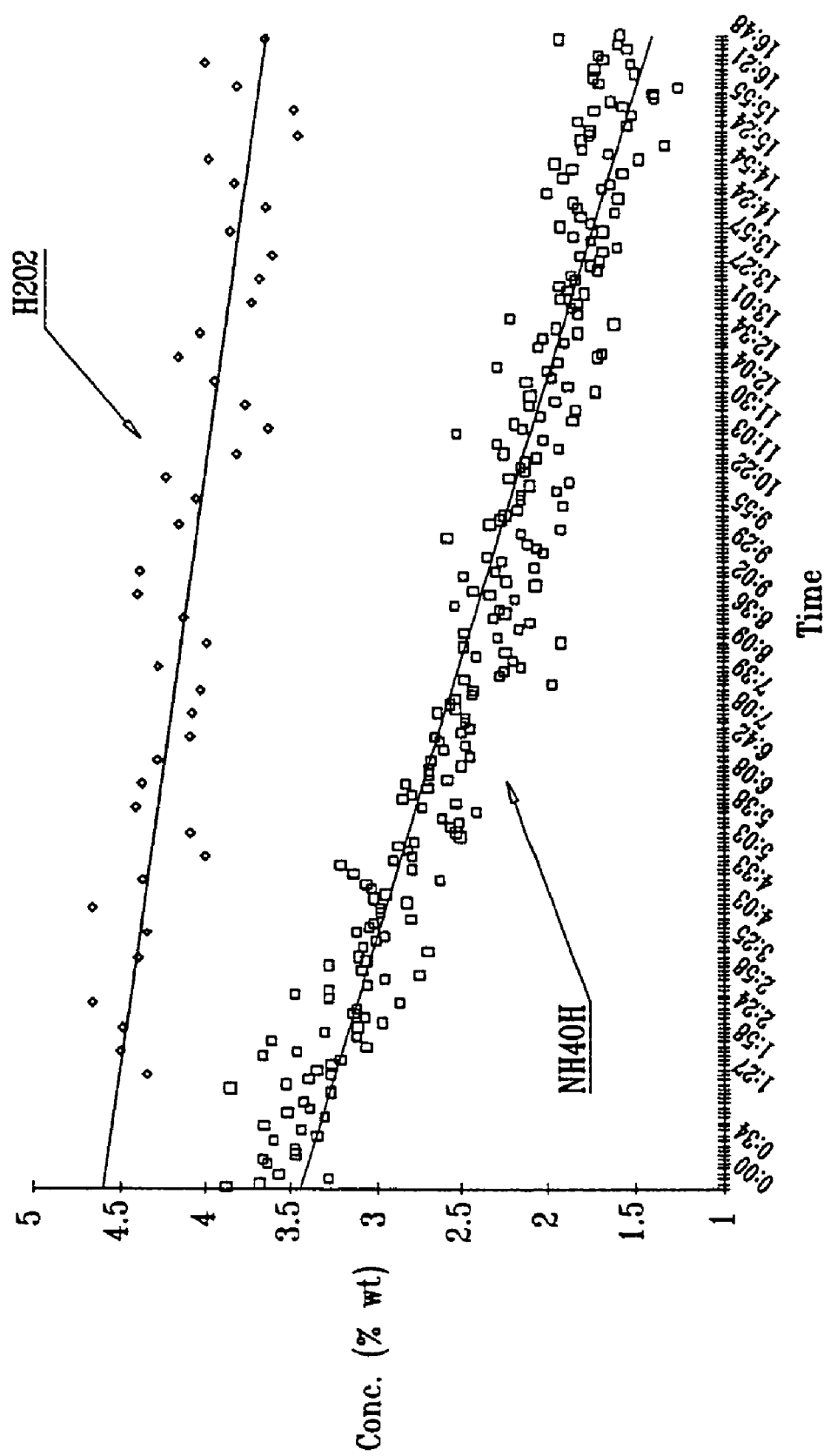

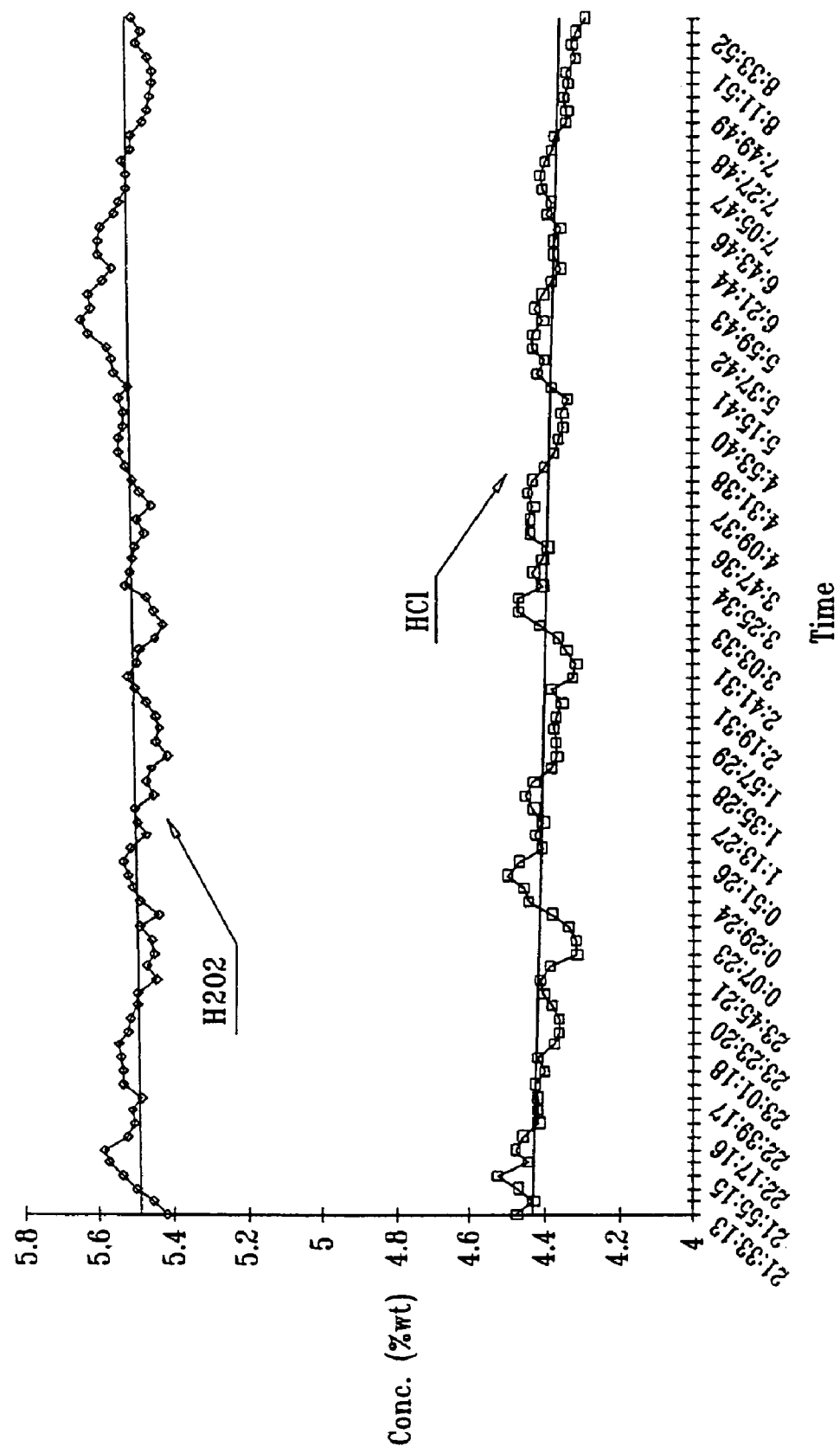

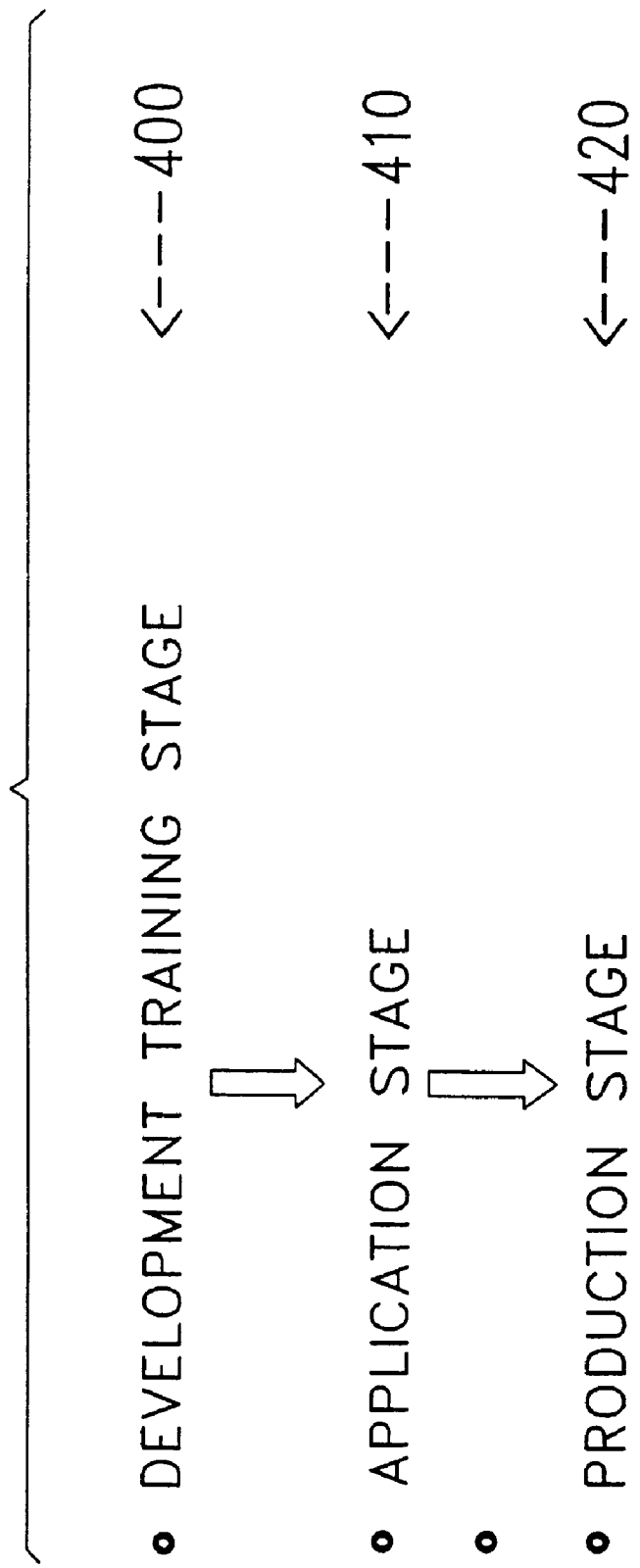

METHOD AND APPARATUS FOR REAL-TIME DYNAMIC CHEMICAL ANALYSIS

FIELD OF THE INVENTION

The present invention relates generally to chemical analysis, and more specifically to methods and apparatus for determining chemical concentrations.

BACKGROUND OF THE INVENTION

In the chemical, semiconductor and biotechnological industries there are many processes which require real-time analysis and control of a reaction. These processes include gas-phase, liquid-phase, mixed phase and solid-state reactions.

In many cases, there are only indirect and off-line methods used to analyze and control a reaction. There is therefore a need to introduce on-line real-time methods and apparatus for analysis and control of such processes.

Instrumental methods including electrochemical and spectroscopic methods for monitoring wet processing have been reported in the following patents which are considered to be representative of the state of the art:

U.S. Pat. No. 5,097,130 to Koashi, et al. describes a quantitative determination method for processing semiconductors and apparatus thereof. U.S. Pat. No. 6,203,659 to Shen, et al. describes a method and apparatus for controlling the quality of a photoresist stripper bath.

U.S. Pat. No. 6,270,986 to Wong describes a method of preserving biological tissue specimens and method of infrared spectroscopic analysis which avoids the effects of polymorphs.

U.S. Pat. No. 5,893,046 to Wu, et al. describes a real time monitor of reacting chemicals in semiconductors manufacturing. This system requires that one must compare each component with a standard, which does not allow real-time analysis of a multicomponent system. This in situ system in the '046 patent further requires that it be inbuilt in the walls of the bath, in which the solution is contained. This sytsem utilizes a bandpass filter for spectral analysis, which typically gives very poor spectral resolution. It not normally possible to identify each of several bath components with such a device simultaneously. The ability to develop complex algorithms employing the output from the bandpass filter is limited.

There is therefore a need to develop a system for real time analysis of multicomponent systems which overcomes the limitations of this prior art.

SUMMARY OF THE INVENTION

It is an object of some aspects of the present invention to provide novel methods and apparatus for real-time ex situ dynamic chemical analysis and identification.

In preferred embodiments of the present invention, improved methods and apparatus are provided for real-time analysis of a chemical. The analysis includes, but is not limited to, determining a concentration of the chemical, a rate of disappearance or appearance of the chemical, and an etch rate of a substance based on the disappearance or appearance of the chemical. The method typically includes passing electromagnetic radiation through a liquid phase in which the chemical is dissolved from an electromagnetic light source, providing a reference beam of electromagnetic radiation, and then performing an ex situ non-contact scanning detection of the electromagnetic radiation of the liquid phase in a near infra-red range (700-2500 nm) by means of a detector so as to provide an optical property of the chemical. The reference beam of the electromagnetic radiation is detected by the detector so as to provide an optical property of the reference beam.

The optical property of the chemical is compared with the optical property of the reference beam by means of a processor so as to provide data concerning the chemical. The processor manipulates the data concerning the chemical by a chemometric manipulation so as to provide a concentration of the chemical. The processor is also operative to provide a rate of disappearance or appearance of the chemical, and an etch rate of a substance based on the disappearance or appearance of the chemical.

The chemometric manipulation typically comprises finding a derivative of a spectrum, calculating waveband changes and band shifting. Typically a model is built for each individual chemical or chemical moiety, and regression analysis is performed for fitting data detected over a period of time to the model.

The regression analysis typically includes at least one of principal component analysis, partial least squares, multiple linear regression, and neural network analysis.

In other preferred embodiments of the present invention, a method and system is described for providing apparatus and a method for the non-contact, in-situ, real-time direct measurement of an etch-rate of silicon oxide in a process bath. The process bath typically comprises 1:5 and 1:50 hydrofluoric acid (HF) or other etching liquids.

Additionally or alternatively, the method may be used to measure a cleaning rate in a cleaning bath, a mixing rate in a mixing bath, or a chemical deposition rate in a deposition bath.

Preferably, the measurement method used is an optical method in the Near Infra-Red (NIR) range with a scanning spectrophotometer, which provides readings of optical density in transmission or reflected mode. Typically, measurement probes are connected from the spectrophotometer by optical fiber sensors which are attached externally via a special adapter to circulation tubes which circulate the bath's liquids. There is no contact of the probes with the chemicals or wafer processing environment. An algorithm translates the measured optical density of the bath content into silicon dioxide etch-rate values and also provides quantitatively the chemical composition of the bath.

In additional preferred embodiments for the present invention, the apparatus, referred to here as an etch-rate meter, is operative to determine etch rate directly and correctly in freshly prepared baths, aged baths and in multi-component baths. The apparatus is further configured to accurately measure dynamic etch rates, both when the circulation is operative and non-operative.

In further preferred embodiments of the present invention, the etch-rate meter is operative to detect and record on-line the addition of chemicals to a bath to which it is connected, either manually or via a CDS. The meter is further operative to detect absence of chemicals, decomposition of non-stable chemicals and circulating pump failure.

In yet further embodiments, the meter may be connected in a closed loop so as to provide a real-time alert if a deviation is detected in process conditions. Similarly, the meter may provide an alert if an addition of a wrong chemical is made, or if there is a fluctuation in a concentration of one or more of the chemicals in the process bath. It may also provide the concentration of each chemical in a multi-component chemical bath system.

In yet further preferred embodiments of the present invention, the etch rate meter eliminates the requirement for using test wafers.

There is thus provided in accordance with a preferred embodiment of the present invention, apparatus for real-time dynamic analysis of a chemical etching process including:

an optical element operative to pass a beam of electromagnetic radiation at least at two points in time through a liquid phase including at least one chemical component and including an etchant, wherein the etchant is operative to etch a solid, a detector operative to perform an ex situ non-contact scanning detection of the electromagnetic radiation subsequent to passing through the liquid phase in a near infra-red range (700-2500 nm) at the at least at two points in time so as to detect a change in an optical property of at least one of the at least one chemical component and the etchant, and a processor operative to activate an algorithm so as to compare the change in the optical property of the at least of the at least one chemical component and the etchant received from the detector so as to provide data concerning a change in concentration of the etchant, and further configured to perform a chemometric manipulation of the data so as to provide a rate of etching of the solid.

Also, in accordance with a preferred embodiment of the present invention, there is provided apparatus wherein the optical element includes:

i) an electromagnetic radiation source operative to transmit electromagnetic radiation in the near infra-red range (700-2500 nm) via a first transmission element through a sampling element adapted to provide a sample of the etchant, and wherein the radiation source is further configured to transmit a reference beam of electromagnetic radiation, ii) a first optical transmission element operative to transmit the electromagnetic radiation from the electromagnetic radiation source to the sample of the etchant, and iii) a second optical transmission element operative to convey the electromagnetic radiation from the sample of the etchant.

Furthermore, in accordance with a preferred embodiment of the present invention, there is provided apparatus wherein the processor is further operative to provide a derivative function of the change concentration of the etchant.

Additionally, in accordance with a preferred embodiment of the present invention, there is provided apparatus wherein the derivative function includes a second order derivative of the change in concentration of the etchant.

Also, in accordance with a preferred embodiment of the present invention, there is provided apparatus wherein the processor is further operative to provide a rate of disappearance of the etchant over a period of time.

Further in accordance with a preferred embodiment of the present invention, there is provided apparatus wherein the processor is further operative to provide a derivative function of the rate of disappearance of the etchant.

Yet further, in accordance with a preferred embodiment of the present invention, there is provided apparatus wherein the etchant is dissolved in a liquid phase.

Still further, in accordance with a preferred embodiment of the present invention, there is provided apparatus wherein the etchant is suspended in the liquid phase.

Also in accordance with a preferred embodiment of the present invention, there is provided apparatus wherein the etchant includes an acid.

Furthermore, in accordance with a preferred embodiment of the present invention, there is provided apparatus wherein the etchant includes a base.

Additionally, in accordance with a preferred embodiment of the present invention, there is provided apparatus wherein the etchant includes a detergent.

Furthermore, in accordance with a preferred embodiment of the present invention, there is provided apparatus, wherein the etchant includes a complexing agent.

Also, in accordance with a preferred embodiment of the present invention, there is provided apparatus wherein the etchant includes at least one ion.

Further, in accordance with a preferred embodiment of the present invention, there is provided apparatus wherein the at least one ion includes at least one positive ion.

Yet further, in accordance with a preferred embodiment of the present invention, there is provided apparatus wherein the at least one positive ion includes a metallic ion.

Still further, in accordance with a preferred embodiment of the present invention, there is provided apparatus wherein the at least one positive ion includes a hydrogen ion.

Also in accordance with a preferred embodiment of the present invention, there is provided apparatus wherein the at least one ion includes at least one negative ion.

Additionally, in accordance with a preferred embodiment of the present invention, there is provided apparatus wherein the negative ion includes at least one of the following, a halide ion, a sulfuric ion, a sulfurous ion, a nitrous ion, a nitric ion, a nitride ion, acetate ion, and persulfate ion.

Also, in accordance with a preferred embodiment of the present invention, there is provided apparatus wherein the etchant is further carried in a gaseous phase to the liquid phase.

Moreover, in accordance with a preferred embodiment of the present invention, there is provided apparatus wherein the first transmission element and the second transmission element do not substantially depress a side-wall of the sampling element.

Additionally, in accordance with a preferred embodiment of the present invention, there is provided apparatus wherein the first transmission element includes a plurality of optical fibers.

Also in accordance with a preferred embodiment of the present invention, there is provided apparatus wherein the sampling element includes a substantially transparent tube adapted to retain a sample of the chemical dissolved in a liquid phase.

Moreover, in accordance with a preferred embodiment of the present invention, there is provided apparatus wherein the substantially transparent tube includes a material transparent to NIR electromagnetic radiation.

Also in accordance with a preferred embodiment of the present invention, there is provided apparatus wherein the material includes at least one of teflon, glass, polyethylene, polypropylene, PET, polyvinylchloride, nylon, Tygon, polystyrene, silicon rubber PVA, and quartz.

Additionally, in accordance with a preferred embodiment of the present invention, there is provided apparatus also including a sampling element including a substantially transparent sampling tube, and wherein the sampling element is further adapted to sample a moving liquid stream in which the etchant is dissolved, wherein the liquid stream flows through the sampling tube.

Also in accordance with a preferred embodiment of the present invention, there is provided apparatus wherein the second optical transmission element includes a plurality of optical fibers.

Further, in accordance with a preferred embodiment of the present invention, there is provided apparatus wherein the optical property is an optical density of absorbance of the electromagnetic radiation.

Yet further, in accordance with a preferred embodiment of the present invention, there is provided apparatus wherein the optical property includes a spectrum of absorbance of the electromagnetic radiation through the etchant.

Still further, in accordance with a preferred embodiment of the present invention, there is provided apparatus wherein the detector includes an optical multiplexer.

Also in accordance with a preferred embodiment of the present invention, there is provided apparatus wherein the optical element is operative to detect a shift in the spectrum over the at least two points in time.

Also in accordance with a preferred embodiment of the present invention, there is provided apparatus wherein the processor is further configured to convert an optical property of each of a plurality of chemical components into a concentration of each of the plurality of chemical components.

Moreover, in accordance with a preferred embodiment of the present invention, there is provided apparatus wherein the processor is further configured to convert a change in an optical property of each of a plurality of chemical components into a rate of change of a concentration of each of the plurality of chemical components.

Also in accordance with a preferred embodiment of the present invention, there is provided apparatus wherein the processor is operative to perform at least one of the following manipulations on the data: principal component analysis, partial least squares analysis, multiple linear regression analysis and neural network analysis.

Additionally, in accordance with a preferred embodiment of the present invention, there is provided apparatus and wherein the optical element is operative in a wet bench.

Furthermore, in accordance with a preferred embodiment of the present invention, there is provided apparatus wherein the optical element is operative in a wet station.

There is thus additionally provided in accordance with another preferred embodiment of the present invention, apparatus for real-time dynamic analysis of a chemical in a bath including:

an optical element operative to dynamically provide an optical property of the chemical, wherein the optical element includes:

i) an electromagnetic radiation source operative to transmit electromagnetic radiation in the near infra-red range (700-2500 nm) over a period of time via a first transmission element through a sampling element adapted to provide a sample of the chemical, and wherein the radiation source is further configured to transmit a reference beam of electromagnetic radiation, ii) a first optical transmission element operative to transmit the electromagnetic radiation from the radiation source to the sample of the chemical over the period of time, iii) a second optical transmission element operative to convey the electromagnetic radiation from the sample of the chemical over the period of time, a detector operative to receive the electromagnetic radiation from the second optical transmission element and further operative to perform an ex situ non-contact scanning detection of the electromagnetic radiation in the near infra-red range over the period of time so as to detect an optical property of the chemical and further configured to receive the reference beam from the electromagnetic radiation source and to detect the optical property of the reference beam of electromagnetic radiation, a processor operative to activate an algorithm so as to compare the optical property of the chemical received from the detector with the optical property of the reference beam received from the detector so as to provide data concerning the chemical over the period of time, and further configured to perform a chemometric manipulation of the data so as to provide a rate of change of concentration of the chemical with a confidence level greater than 95%, independent of the age of the bath, and a reporter element operative to report the rate of change of the concentration of the chemical.

Also in accordance with a preferred embodiment of the present invention, there is provided apparatus wherein the reporter element includes a display.

Additionally, in accordance with a preferred embodiment of the present invention, there is provided apparatus wherein the reporter element includes a printer.

There is thus provided in accordance with another preferred embodiment of the present invention, apparatus for real-time analysis of a rate of change of concentration of a chemical in a bath including:

an optical element operative to provide an optical property of the chemical, wherein the optical element includes:

i) an electromagnetic radiation source operative to transmit electromagnetic radiation in the near infra-red range (700-2500 nm) via a first transmission element through a sampling element adapted to provide a sample of the chemical, ii) a first optical transmission element operative to transmit the electromagnetic radiation from the radiation source to the sample of the chemical, iii) a second optical transmission element operative to convey the electromagnetic radiation from the sample of the chemical, a detector operative to receive the electromagnetic radiation from the second optical transmission element and further operative to perform an ex situ non-contact scanning detection of the electromagnetic radiation in the near infra-red range over the period of time, and a processor operative to activate an algorithm so as to compare the optical property of the chemical received from the detector with the optical property of the reference beam received from the detector so as to provide data concerning the chemical over the period of time, and further configured to perform a chemometric manipulation of the data so as to provide a change in concentration of the chemical over the period of time with a confidence level greater than 95%, independent of the age of the bath.

Additionally, in accordance with a preferred embodiment of the present invention, there is provided apparatus wherein the sampling element includes an attaching device, the attaching device is operative to attach at least one of the first optical transmission element and the second optical transmission element to a sample tube without squeezing the tube in such a way that there is generally no space remaining between the at least one of the first optical transmission element and the second optical transmission element and at least one external wall of the sample tube.

Additionally, in accordance with a preferred embodiment of the present invention, there is provided apparatus wherein the detector includes a near-infra-red scanning spectrometer, and wherein the spectrometer is operative to record a spectrum and further operative to continuously measure an optical density of a liquid flowing in a tube of the sampling element.

Additionally, in accordance with a preferred embodiment of the present invention, there is provided apparatus wherein the apparatus is integrated into a semiconductor processing wet station.

Furthermore, in accordance with a preferred embodiment of the present invention, there is provided apparatus wherein the optical element is operative in a wet bench.

Moreover, in accordance with a preferred embodiment of the present invention, there is provided apparatus wherein the optical element is operative in a wet station.

Additionally, in accordance with a preferred embodiment of the present invention, there is provided apparatus wherein the spectrometer is further configured to provide the change in the concentration of the chemical to a control device of the wet station.

Further, in accordance with a preferred embodiment of the present invention, there is provided apparatus and wherein the control device is further configured to add a quantity of the chemical to a bath in the wet station in order to effect a change in the concentration of the chemical in the bath.

Yet further, in accordance with a preferred embodiment of the present invention, there is provided apparatus further including an alarm.

Still further, in accordance with a preferred embodiment of the present invention, there is provided apparatus wherein the alarm provides an indication of the concentration of the chemical in the bath wherein the concentration deviates beyond a preset limit.

Additionally, in accordance with a preferred embodiment of the present invention, there is provided apparatus further including a chemical correction system configured to correct the concentration of the chemical in the bath.

Also, in accordance with a preferred embodiment of the present invention, there is provided apparatus wherein the chemical correction system is operative to add a solvent to the bath.

Additionally, in accordance with a preferred embodiment of the present invention, there is provided apparatus wherein the solvent includes water.

Also, in accordance with a preferred embodiment of the present invention, there is provided apparatus wherein the solvent is a non-aqueous solvent.

Additionally, in accordance with a preferred embodiment of the present invention, there is provided apparatus wherein the chemical correction system includes a replenisher operative to replenish the chemical so as to provide the bath with the concentration with the preset limit.

Furthermore, in accordance with a preferred embodiment of the present invention, there is provided apparatus wherein the detector is further operative to detect if a second chemical has been added to the bath in place of the chemical and the processor is further operative to provide an indication of the second chemical.

Additionally, in accordance with a preferred embodiment of the present invention, there is provided apparatus wherein the alarm is further operative to provide an indication of the presence of the second chemical.

Moreover, in accordance with a preferred embodiment of the present invention, there is provided apparatus further configured to simultaneously measure a plurality of chemical components of the bath.

Additionally, in accordance with a preferred embodiment of the present invention, there is provided apparatus further configured to measure the plurality of chemical components in the bath with a confidence level of more than 95%, independent of the age of the bath.

Also, in accordance with a preferred embodiment of the present invention, there is provided apparatus wherein the plurality of chemical components includes multiple etching components.

Moreover, in accordance with a preferred embodiment of the present invention, there is provided apparatus wherein the confidence level is independent of a by-product produced by the etching components.

Additionally, in accordance with a preferred embodiment of the present invention, there is provided apparatus further operative to detect a malfunctioning of a circulating pump of the bath.

Also, in accordance with a preferred embodiment of the present invention, there is provided apparatus further operative to detect a fault in a rate of addition of a replenishing chemical.

Moreover, in accordance with a preferred embodiment of the present invention, there is provided apparatus further operative to detect a bubble.

Also, in accordance with a preferred embodiment of the present invention, there is provided apparatus further configured to measure the concentration of the plurality of chemical components in the bath with a confidence level of more than 95%, independent of a presence of bubbles in the bath.

Additionally, in accordance with a preferred embodiment of the present invention, there is provided apparatus further configured to provide the change in the concentration of the chemical over the period of time with a confidence level of greater than 95%, independent of the process temperature.

Also, in accordance with a preferred embodiment of the present invention, there is provided apparatus operative to detect at least one of the following: $HF:H_2O$, 1:5, HF1:50, buffered oxide etch (BOE), $H_2SO_4:HNO_3:HF$, EG+HF, Acetic Acid: $NH_4F$, $H_3PO_4:HNO_3$:Acetic acid, $HNO_3$:HF, an acid, a base, a commercial oxide etchant, a commercial silicon etchant and a commercial metallic etchant.

Additionally, in accordance with a preferred embodiment of the present invention, there is provided apparatus operative to detect at least one of the following: $H_2SO_4:H_2O_2$, $H_2SO_4:HNO_3$ and $H_2SO_4$:PERSULPHATE.

There is thus also provided in accordance with another preferred embodiment of the present invention, apparatus for real-time analysis of an etch rate of a substance in a bath including:

an optical element operative to provide an optical property of a chemical, wherein the optical element includes:

i) an electromagnetic radiation source operative to transmit electromagnetic radiation in the near infra-red range (700-2500 nm) via a first transmission element through a sample of the chemical over a period of time, and further configured to transmit a reference beam of electromagnetic radiation, ii) a first optical transmission element operative to transmit the electromagnetic radiation from the electromagnetic radiation source to the sample of the chemical, iii) a second optical transmission element operative to convey the electromagnetic radiation from the sample of the chemical, a detector operative to receive the electromagnetic radiation from the second optical transmission element and further operative to perform an ex situ non-contact scanning detection of the electromagnetic radiation in the near infra-red range over the period of time and further configured to receive the reference beam from the electromagnetic radiation source and to detect the optical property of the reference beam of electromagnetic radiation, and a processor operative to compare the optical property of the chemical over the period of time received from the detector with the optical property of the reference beam received from the detector so as to provide a data concerning the chemical, and further configured to perform a chemometric manipulation of the data so as to provide a change in the concentration of the chemical over the period of time with a confidence level greater than 95%, independent of the age of the bath, and further adapted to convert the change in the concentration of the chemical into a rate of etching of the substance.

There is thus additionally provided in accordance with another preferred embodiment of the present invention, apparatus substantially as described in the specification.

There is thus further provided in accordance with another preferred embodiment of the present invention, apparatus substantially as shown in the figures.

There is thus still further provided in accordance with another preferred embodiment of the present invention, a method for real-time analysis of a chemical etching process including:

passing electromagnetic radiation through a liquid phase, including an etchant, at least at two points in time from an electromagnetic light source, wherein the etchant is operative to etch a solid, performing an ex situ non-contact scanning detection of the electromagnetic radiation passed through the liquid phase, in a near infra-red range (700-2500 nm) by means of a detector at the at least at two points in time so as to detect a change in an optical property of the liquid phase, comparing the optical property of the at least two points in time by means of an algorithm in a processor so as to provide data concerning the etchant, and manipulating the data concerning the etchant by a chemometric manipulation by means of the processor so as to provide a rate of etching of the solid.

There is thus yet further provided in accordance with another preferred embodiment of the present invention, a method wherein the passing includes:

i) transmitting electromagnetic radiation in the near infra-red range (700-2500 nm) from an electromagnetic radiation source via a first transmission element through a sampling element, the sampling adapted to provide a sample of the liquid phase, ii) transmitting the electromagnetic radiation via a first optical transmission element from the electromagnetic radiation source to the sample of the liquid phase, iii) conveying the electromagnetic radiation from the sample of the chemical via a second optical transmission element, and receiving the electromagnetic radiation from the second optical transmission element by a detector.

Additionally, in accordance with a preferred embodiment of the present invention, there is provided a method wherein the processor is further operative to provide a differential rate of change of the etching of the solid over a period of time.

Also, in accordance with a preferred embodiment of the present invention, there is provided a method wherein wherein the processor is further operative to provide a rate of disappearance of the etchant over a period of time.

Furthermore, in accordance with a preferred embodiment of the present invention, there is provided a method wherein the processor is further operative to provide a rate of etching of a solid as a function of the concentration of the etchant.

Additionally, in accordance with a preferred embodiment of the present invention, there is provided a method wherein and wherein the etchant is suspended in the liquid phase.

Also, in accordance with a preferred embodiment of the present invention, there is provided a method wherein the etchant is dissolved in the liquid phase.

Furthermore, in accordance with a preferred embodiment of the present invention, there is provided a method wherein the etchant includes an acid.

Additionally, in accordance with a preferred embodiment of the present invention, there is provided a method wherein the etchant includes a base.

Further, in accordance with a preferred embodiment of the present invention, there is provided a method wherein the etchant includes a detergent.

Yet further, in accordance with a preferred embodiment of the present invention, there is provided a method wherein the etchant includes a complexing agent.

Additionally, in accordance with a preferred embodiment of the present invention, there is provided a method wherein the etchant includes a metallic compound.

Still further, in accordance with a preferred embodiment of the present invention, there is provided a method wherein the etchant includes at least one ion.

Additionally, in accordance with a preferred embodiment of the present invention, there is provided a method wherein the at least one ion includes at least one positive ion.

Also, in accordance with a preferred embodiment of the present invention, there is provided a method wherein the at least one positive ion includes a metallic ion.

Furthermore, in accordance with a preferred embodiment of the present invention, there is provided a method wherein the at least one positive ion includes a hydrogen ion.

Additionally, in accordance with a preferred embodiment of the present invention, there is provided a method wherein the at least one ion includes at least one negative ion.

Moreover, in accordance with a preferred embodiment of the present invention, there is provided a method wherein the negative ion includes at least one of the following, a halide ion, a sulfuric ion, a sulfurous ion, a nitrous ion, a nitric ion, and a nitride ion.

Additionally, in accordance with a preferred embodiment of the present invention, there is provided a method wherein the etchant is carried to the solid in a gaseous phase.

Further, in accordance with a preferred embodiment of the present invention, there is provided a method wherein the sampling element includes a substantially transparent sampling tube, and wherein the sampling element samples a moving liquid stream in which the etchant is dissolved, wherein the liquid stream flows through the sampling tube.

Yet further, in accordance with a preferred embodiment of the present invention, there is provided a method wherein the optical property is an optical density of absorbance of the electromagnetic radiation.

Still further, in accordance with a preferred embodiment of the present invention, there is provided a method wherein the optical property includes a spectrum of absorbance of the electromagnetic radiation through the etchant.

Additionally, in accordance with a preferred embodiment of the present invention, there is provided a method wherein the comparing further includes detecting a shift in the spectrum over a period of time.

Also, in accordance with a preferred embodiment of the present invention, there is provided a method wherein the manipulating further includes converting an optical density measurement of the etchant into a concentration parameter of the etchant.

Moreover, in accordance with a preferred embodiment of the present invention, there is provided a method wherein the manipulating further includes converting an optical property of each of a plurality of chemicals into a concentration of each of the plurality of chemicals.

Further, in accordance with a preferred embodiment of the present invention, there is provided a method wherein the converting further includes converting the change in an optical property of each of the plurality of chemicals into a respective rate of change of a concentration of each of the plurality of chemicals.

There is thus provided in accordance with another preferred embodiment of the present invention, a method for determining etch rate of a solid in a process bath by NIR in a liquid-phase sample including at least one chemical component and at least one etchant, including:

a) obtaining a plurality of liquid phase samples each including at least one chemical component and at least one etchant, and wherein each sample has a etch rate determined by thickness measurements, b) irradiating the plurality of liquid phase samples with NIR and recording their respective spectral scanning transmission intensities over the NIR range (700-2500 nm), c) comparing variations of their respective spectral scanning transmission intensities over the NIR range (700-2500 nm) so as to correlate spectral transmission of the plurality of samples with the etch rate determined by thickness measurements, d) developing a calibration model based on the results of step (c), e) measuring scanning spectral transmission over the NIR range of a further liquid phase sample including at least one chemical component and at least one etchant, and f) determining at least one of an etch rate and a concentration of the at least one chemical component and at least one etchant of the further liquid phase sample based on the calibration model.

There is thus further provided in accordance with another preferred embodiment of the present invention, a method for dynamic real-time analysis of an etching process including:

providing an optical property of a chemical component of the process over a period of time by means of an optical element, detecting the optical property of the chemical component of the process by means of a detector during the period of time, comparing the optical property of the chemical component during the period of time by means of an algorithm in a processor so as to provide a change in a concentration of the chemical component.

There is thus also provided in accordance with another preferred embodiment of the present invention, a method for real-time analysis of a rate of change of concentration of a chemical in a bath, including:

providing an optical property of the chemical, detecting the optical property of the chemical in a near infra-red range over a period of time, and processing the optical property of the chemical over the period of time by means of an algorithm so as to provide a change in the concentration of the chemical over the period of time with a confidence level greater than 95%, independent of an age of the bath.

Additionally, in accordance with a preferred embodiment of the present invention, there is provided a method further including providing the change in the concentration of the chemical to a control device of a wet station.

Also, in accordance with a preferred embodiment of the present invention, there is provided a method further including adding a quantity of at least one of the chemical and water to a bath in the wet station so as to effect a change in the concentration of the chemical in the bath.

Moreover, in accordance with a preferred embodiment of the present invention, there is provided a method further including providing an alarm signal responsive to an indication of the concentration of the chemical in the bath, wherein the concentration deviates beyond a preset limit.

Additionally, in accordance with a preferred embodiment of the present invention, there is provided a method wherein the adding includes adding a solvent to the bath.

Also, in accordance with a preferred embodiment of the present invention, there is provided a method wherein the solvent is water.

Furthermore, in accordance with a preferred embodiment of the present invention, there is provided a method wherein the solvent is a non-aqueous solvent.

Moreover, in accordance with a preferred embodiment of the present invention, there is provided a method wherein the adding includes replenishing the chemical so as to provide the bath with the concentration within the preset limit.

Additionally, in accordance with a preferred embodiment of the present invention, there is provided a method wherein the detecting includes detecting if a second chemical has been added to a bath in place of the chemical and further providing an indication of the second chemical.

Also, in accordance with a preferred embodiment of the present invention, there is provided a method further including simultaneously measuring a plurality of chemical components of a bath.

Moreover, in accordance with a preferred embodiment of the present invention, there is provided a method further including measuring the concentration of the plurality of chemical components in the bath with a confidence level of more than 95%, independent of the age of the bath.

Further, in accordance with a preferred embodiment of the present invention, there is provided a method wherein the plurality of chemical components includes multiple etching components.

Additionally, in accordance with a preferred embodiment of the present invention, there is provided a method wherein the confidence level of at least one of the concentration of the chemical and an etch rate is independent of a by-product produced by the etching components.

Also, in accordance with a preferred embodiment of the present invention, there is provided a method wherein the detecting includes detecting a malfunctioning of a circulating pump of the bath.

Further, in accordance with a preferred embodiment of the present invention, there is provided a method wherein the detecting includes detecting a fault in a rate of addition of a replenishing chemical.

Additionally, in accordance with a preferred embodiment of the present invention, there is provided a method wherein the detecting includes detecting a bubble.

Still further, in accordance with a preferred embodiment of the present invention, there is provided a method wherein the detecting includes measuring a concentration of the plurality of chemical components in the bath with a confidence level of more than 95%, independent of a presence of bubbles in the bath.

Yet further, in accordance with a preferred embodiment of the present invention, there is provided a method including providing the change in the concentration of the chemical over the period of time with a confidence level of greater than 95%, independent of the process temperature.

Additionally, in accordance with a preferred embodiment of the present invention, there is provided a method wherein the detecting includes detecting at least one of the following: HF:H$_2$O, HF1:5, HF1:50, BOE, H2SO$_4$:HNO$_3$:HF, EG+HF, Acetic Acid: NH$_4$F, H3PO$_4$:HNO$_3$:Acetic acid, HNO$_3$:HF, an acid, a base, a commercial oxide etchant, a commercial silicon etchant and a commercial metallic etchant.

Additionally, in accordance with a preferred embodiment of the present invention, there is provided a method wherein the detecting includes detecting at least one of the following H$_2$SO$_4$:H$_2$O$_2$, H$_2$SO$_4$:HNO$_3$ and H$_2$SO$_4$:PERSULPHATE.

There is thus also provided in accordance with another preferred embodiment of the present invention, a method substantially as described in the specification.

There is thus further provided in accordance with another preferred embodiment of the present invention, a method substantially as shown in the figures.

There is thus yet further provided in accordance with another preferred embodiment of the present invention, a computer program product, the product including a computer-readable medium having program instructions embodied therein, which instructions, when read by a computer, cause the computer to:

provide an optical property of a chemical in a bath, detect the optical property of the chemical in a near infra-red range over a period of time, and process the optical property of the chemical over the period of time by means of an algorithm so as to provide a change in the concentration of the chemical over the period of time with a confidence level greater than 95%, independent of the age of the bath.

There is thus also provided in accordance with another preferred embodiment of the present invention, a computer program product, the product including a computer-readable medium having program instructions embodied therein, which instructions, when read by a computer, cause the computer to:

provide an optical property of a chemical component of a process over a period of time by means of an optical element, detect the optical property of the chemical component of the process by means of a detector during the period of time, compare the optical property of the chemical component during the period of time by means of an algorithm in a processor so as to provide a change in a concentration of the chemical component.

There is thus also provided in accordance with another preferred embodiment of the present invention, a computer program product, the product including a computer-readable medium having program instructions embodied therein, which instructions, when read by a computer, cause the computer to:

pass electromagnetic radiation through a liquid phase, including an etchant, at least at two points in time from an electromagnetic light source, wherein the etchant is operative to etch a solid, perform an ex situ non-contact scanning detection of the electromagnetic radiation passed through the liquid phase, in a near infra-red range (700-2500 nm) by means of a detector at the at least at two points in time so as to detect a change in an optical property of the liquid phase, compare the optical property of the at least two points in time by means of an algorithm in a processor so as to provide data concerning the etchant, and manipulate the data concerning the etchant by a chemometric manipulation by means of the processor so as to provide a rate of etching of the solid.

There is thus also provided in accordance with another preferred embodiment of the present invention, a calibration model for determining etch rate of a solid in a process bath by NIR in a liquid-phase sample including at least one chemical component and at least one etchant, including:

a) obtaining a plurality of liquid phase samples each including at least one chemical component and at least one etchant, and wherein each sample has a etch rate determined by thickness measurements, b) irradiating the plurality of liquid phase samples with NIR and recording their respective spectral scanning transmission intensities over the NIR range (700-2500 nm), c) comparing variations of their respective spectral scanning transmission intensities over the NIR range (700-2500 nm) so as to correlate spectral transmission of the plurality of samples with the etch rate determined by thickness measurements, d) developing a calibration model based on the results of step (c), e) measuring scanning spectral transmission over the NIR range of a further liquid phase sample including at least one chemical component and at least one etchant, and f) determining at least one of an etch rate and a concentration of the at least one chemical component and at least one etchant of the further liquid phase sample based on the calibration model.

The present invention will be more fully understood from the following detailed description of the preferred embodiments thereof, taken together with the drawings, in which:

BRIEF DESCRIPTION OF THE DRAWINGS

FIG. 2 is a simplified pictorial illustration showing further details of a sample tube and a pair of probes in the NIR measurement system of FIG. 1;

Figure 9:
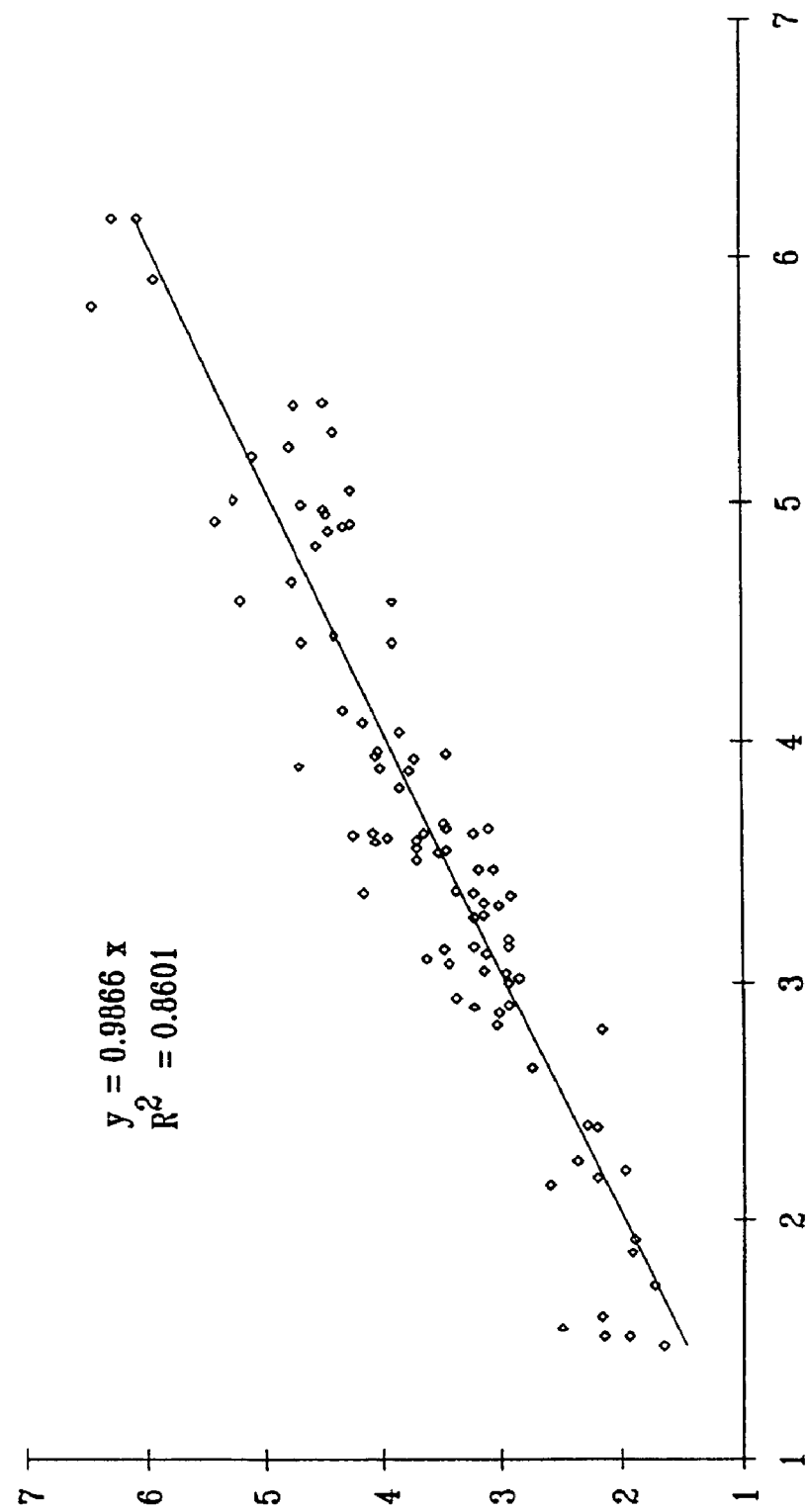
Figure 10:
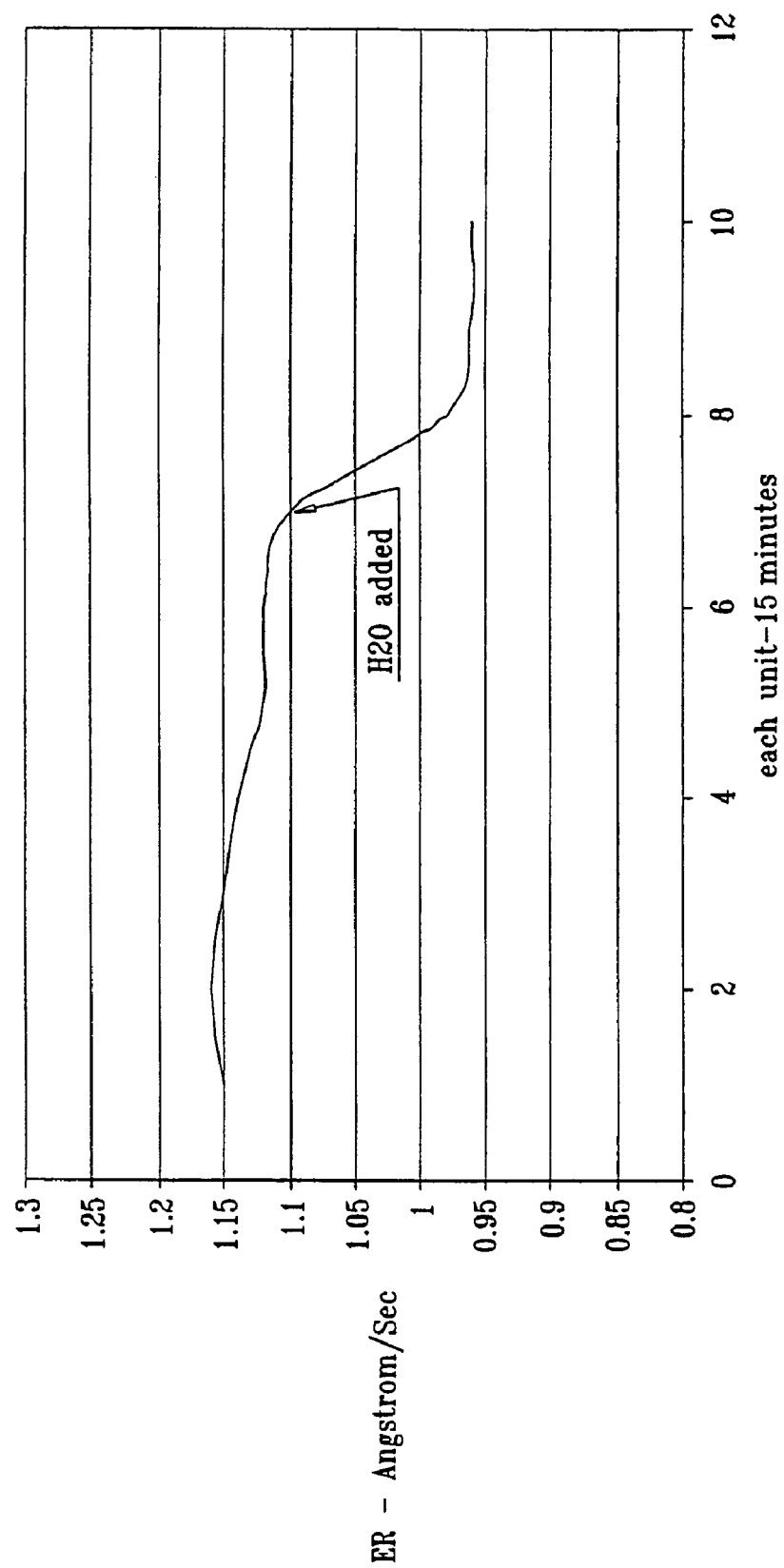
Figure 11:
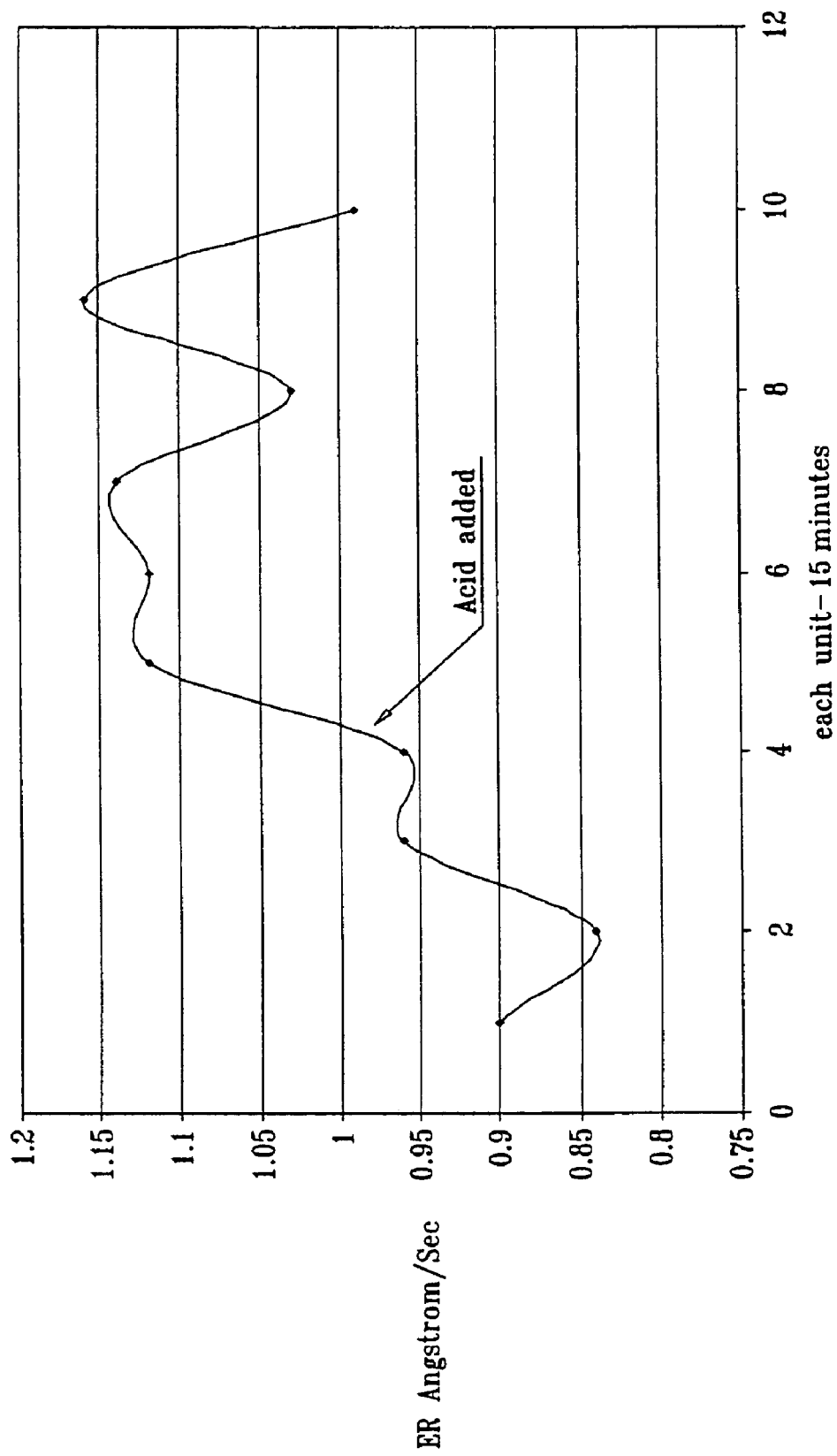
Figure 12:
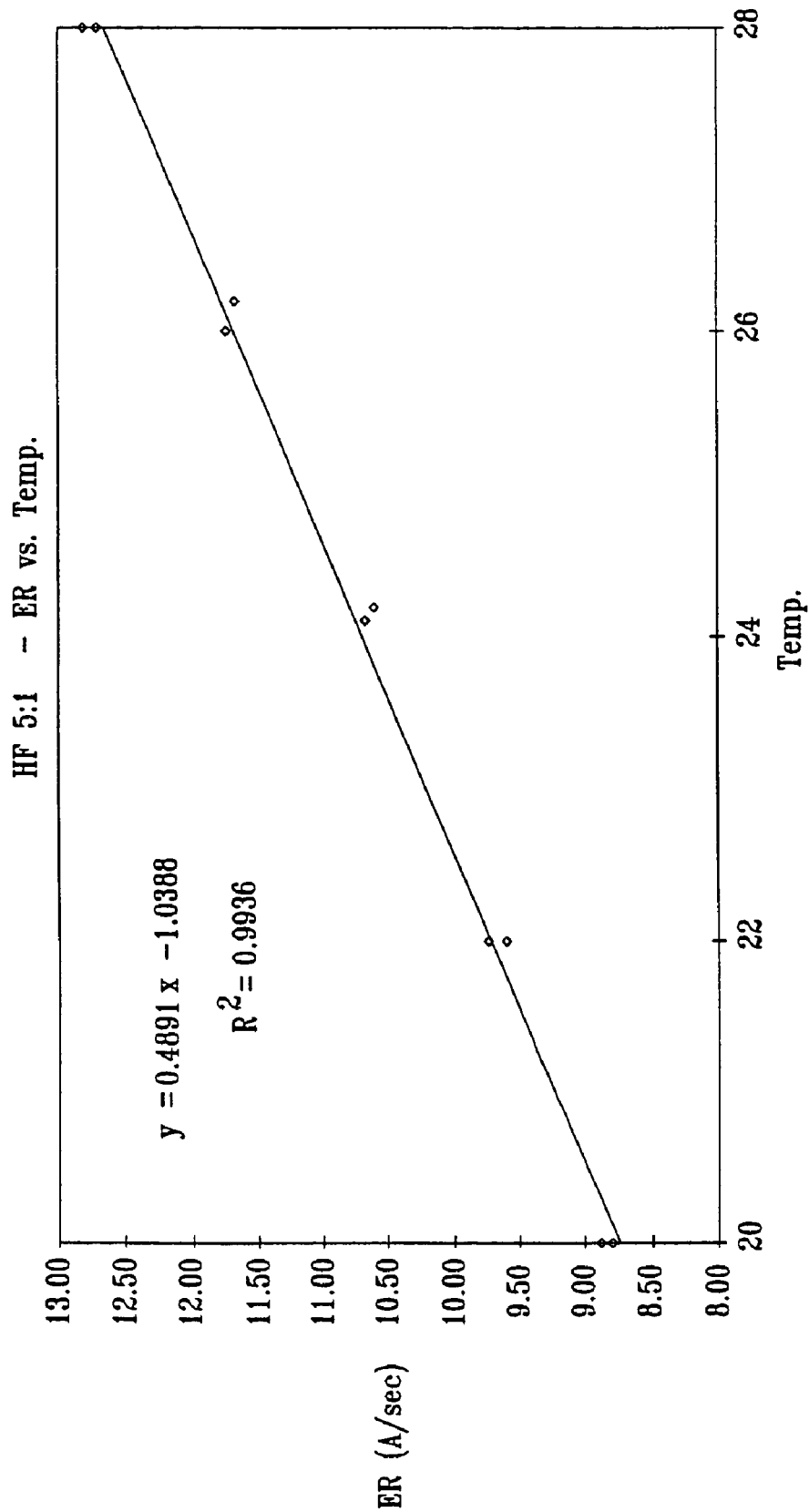
Figure 13:
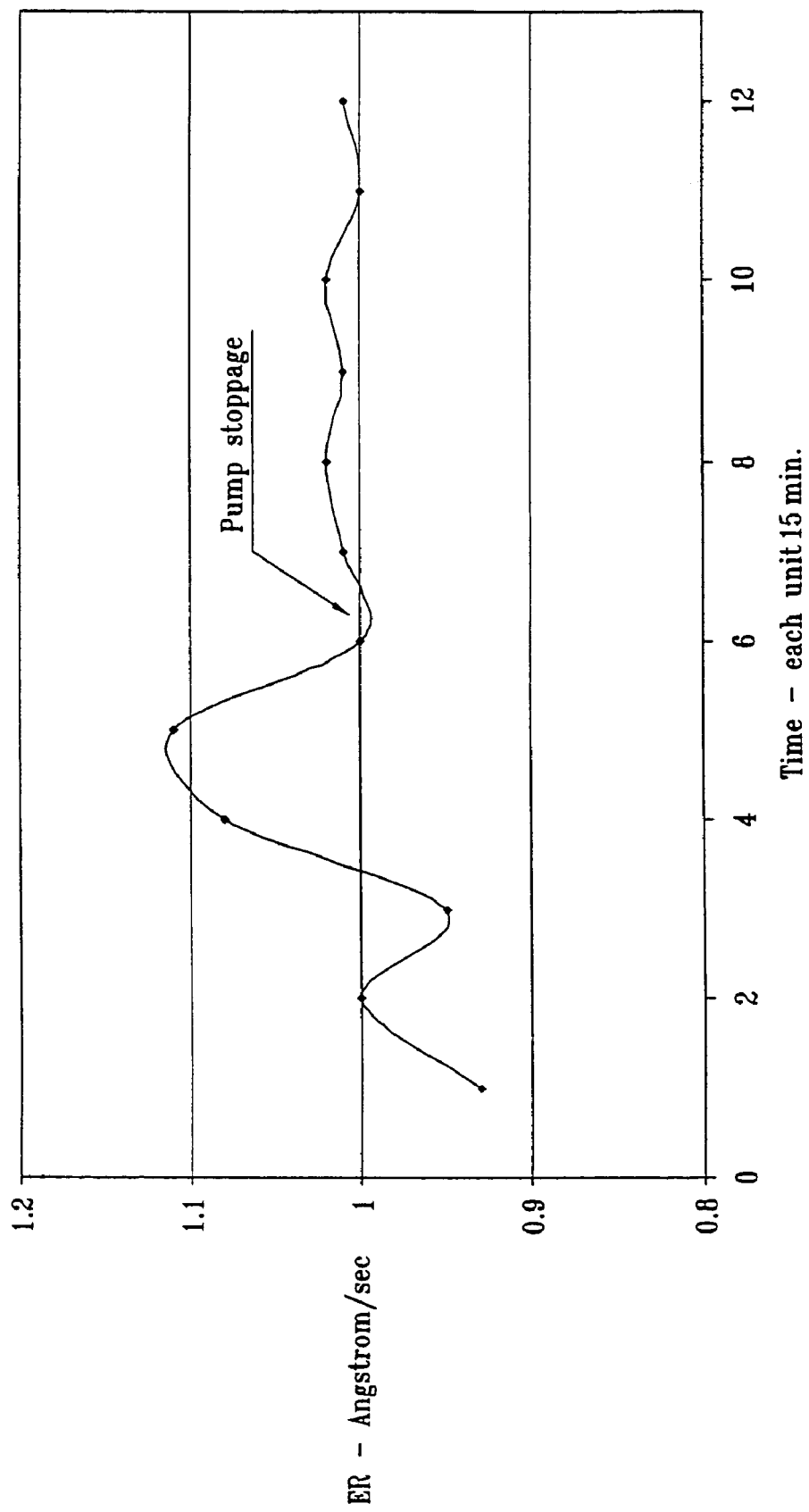
Figure 14:
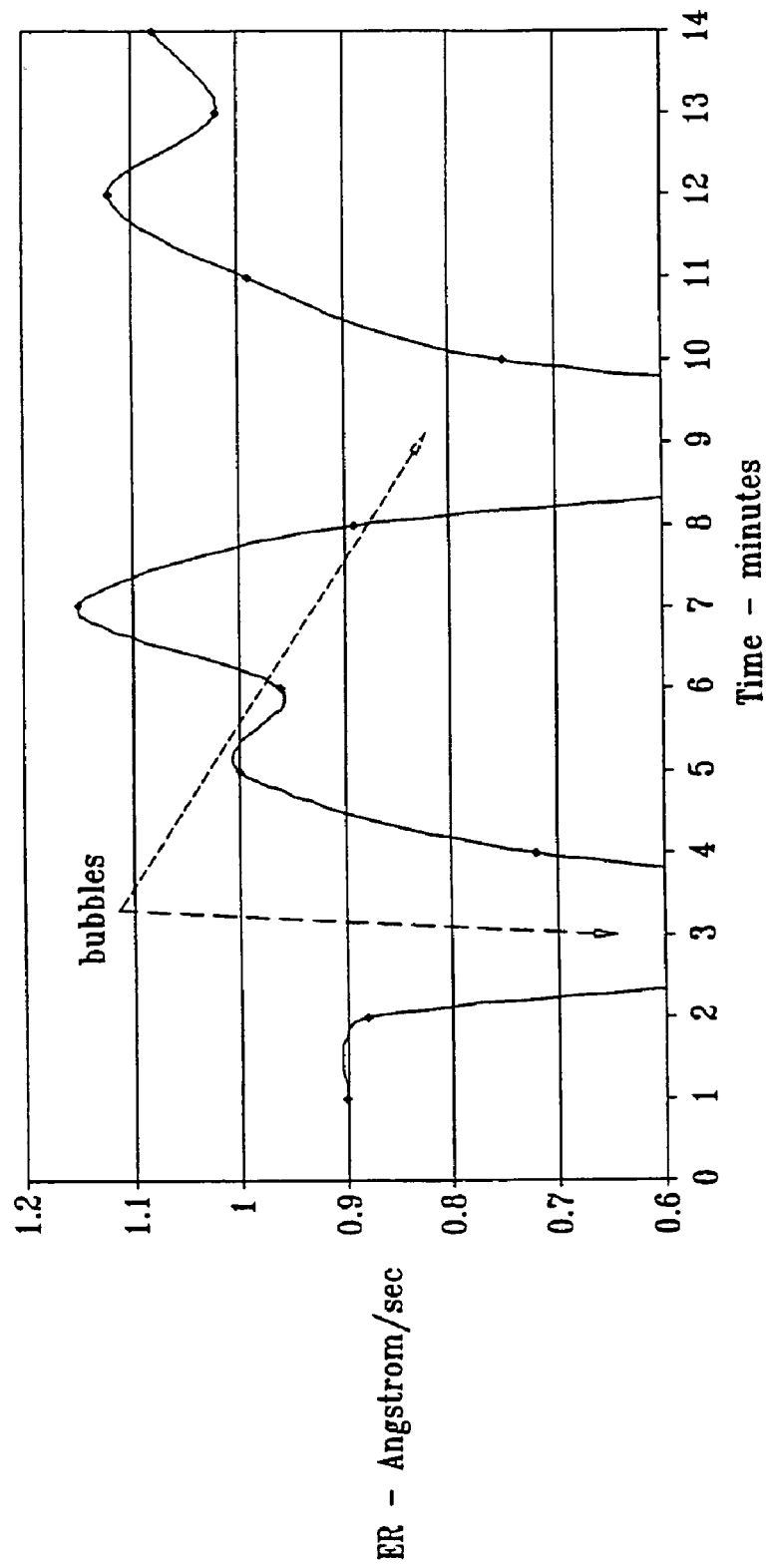

FIG. 9 is a calibration curve of the concentration by hydrogen peroxide in bath SC1 (FIG. 3) measured by an etch-rate meter, in accordance with a preferred embodiment of the present invention;

FIG. 10 is a graph showing the effect of a water addition on the etch rate measured by an etch-rate meter, in accordance with a preferred embodiment of the present invention;

FIG. 11 is a graph showing the effect of a hydrofluoric acid addition on the etch rate measured by an etch-rate meter, in accordance with a preferred embodiment of the present invention;

FIG. 12 is a graph displaying a correlation of the effect of temperature on an etch rate measured by an etch-rate meter, in accordance with a preferred embodiment of the present invention;

FIG. 13 is a graph displaying a correlation of the effect of stopping a circulating pump of a process bath on an etch rate as a function of time measured by an etch-rate meter, in accordance with a preferred embodiment of the present invention;

FIG. 14 is a graph displaying a correlation of the effect of bubbles in the sample tube as a function of time on an etch rate measured by an etch-rate meter, in accordance with a preferred embodiment of the present invention;

FIG. 15 is a simplified time chart of measurements of etch rate made by an etch meter compared to those made with test wafers, in accordance with a preferred embodiment of the present invention;

FIGS. 16A and 16B are simplified charts displaying a concentration of two components in a SC1 and SC2 process bath measured by an etch meter, in accordance with a preferred embodiment of the present invention; and FIG. 17 is a simplified flowchart for the methodology of development of the chemometric-based algorithm according to a preferred embodiment of the present invention.

DETAILED DESCRIPTION OF PREFERRED EMBODIMENTS

The methods and apparatus described herein are for real-time analysis of a chemical. The analysis includes, but is not limited to, determining a concentration of the chemical, a rate of disappearance or appearance of the chemical, and an etch rate of a substance based on the disappearance or appearance of the chemical. These are exemplified by, but are not limited to, an etching process.

Typically, one of the main goals of an etching process is to etch an item at a known and controlled etch rate. This enables transfer of an exact circuit pattern from the mask/reticule onto the wafer surface. Similarly, control of other processes such as wafer cleaning and surface preparation is critical to the production of the wafer or components therein.

Figure 1:
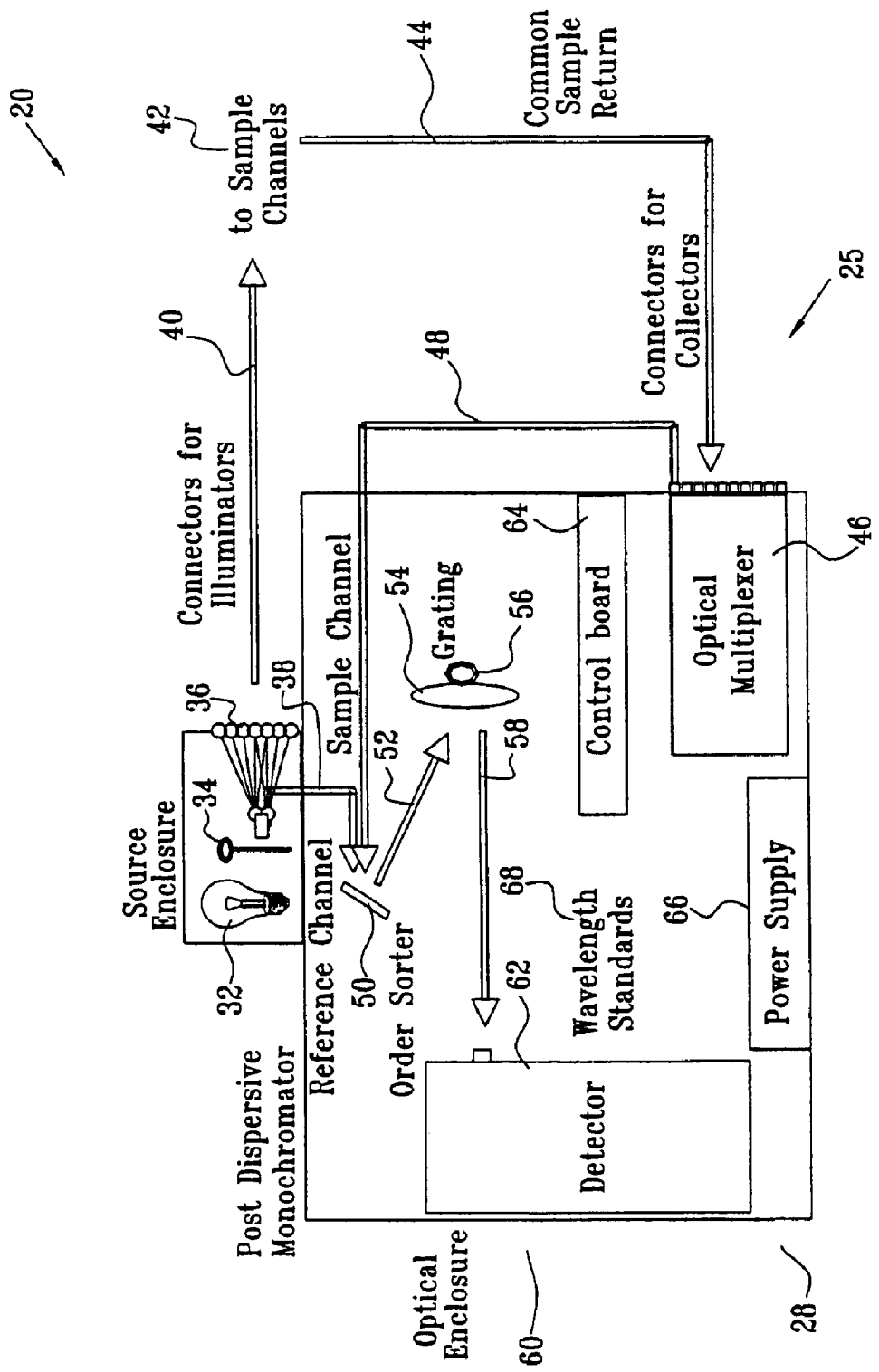
FIG. 1 is a simplified pictorial illustration showing a system for analysis of a chemical sample employing a near infra-red (NIR) measurement system in accordance with a preferred embodiment of the present invention.

Reference is now made to FIG. 1, which is a simplified pictorial illustration showing a system 20 for analysis of a chemical sample employing a near infra-red (NIR) measurement system in accordance with a preferred embodiment of the present invention. System 20 comprises a spectrophotometer system 25, a radiation source enclosure 30, including an electromagnetic radiation source 32, a monochromator 34, a main channel 36 for transfer of the radiation to a first fiber optic probe 40. Monochromator 34 also provides a reference channel of the electromagnetic radiation to an optical enclosure 60. The first fiber optic probe transfers the radiation to at least one sample channel 42. Sample channel 42 is described in further detail in FIG. 2 hereinbelow. A second fiber optic probe 44 transfers the electromagnetic radiation from sample channel 42 to the optical enclosure. An optical multiplexer 46 is operative to receive signals of electromagnetic radiation from a multiplicity of probes such as probe 44. Multiplexer 46 transfer the electromagnetic radiation from to a mirror 50 which reflects the radiation to a lens 54, held by a grating 56. The radiation is transferred from lens 54 to a detector 62. The detector is operative receive the incoming electromagnetic radiation from an order sorter 59 and to receive wavelength standards from a wavelength standard's element 68. The detector provides an output of data or optical densities of the chemical over a spectral range, such as the near infrared range (700-2500 nm). A processor 64 receives the data or optical density of the chemical from detector 62 as well as the data or optical density of the reference beam. Typically, the processor performs several operations. Generally it provides a optical density value of that of the chemical minus the optical density of the reference beam. The processor also performs a chemometric manipulation of data received from detector 62.

Near Infrared Analysis

Near infra red (NIR) is the analytical technique used in the development of system 20 (an Etch Rate Meter) of the present invention. NIR is a spectroscopic technique based upon absorption bands observed at 700-2500 nm. These bands are due to chemical bond vibrations, overtones and their combinations. NIR analytical techniques are used for inorganic and organic species in aqueous and non-aqueous matrix and in gaseous, liquid, solids states. This technique may be used for qualitative i.e. identification of chemical species and whole matrix and quantitative i.e. determination of concentration of an analyte in a given matrix. It is also used for obtaining physical information such as: density, viscosity and texture of the sample matrix. Performance parameters of the matrix such as, octane number of fuels, ruminants feed digestibility etc. may be also quantified by using NIR spectrum (ref. 5).

An NIR spectrometer may be used for ex situ analytical methods in wet processing, and provides potentially great benefits using fiber optic probes for remote sensing, and in-line process sensors may be implemented.

In order to obtain precise measurements and accurate analytical work, it is important to use a scanning spectrometer, such as a high quality NIR spectrometer. This should have a spectral resolution of at least 2 nm and instrumental noise should preferably be in the range of milli-Absorbance units. This is in opposition to a single wavelength filter photometer in a multi filter spectrophotometer with a broad spectral resolution, which produces only a non-continuous spectrum with only several discrete wavelengths. Such a non-continuous NIR spectrum is not typically capable of overcoming the problems of very high precision and accuracy in qualitative and quantitative analysis. Furthermore, such single wavelength filters in a multi-filter photometer are inferior for chemometric manipulations of the spectra, such as derivitization.

Analysis of a wet etching aqueous media with a scanning NIR spectrometer may be achieved utilizing the entire spectral range. Most important for this application are the OH stretch bands in all overtones and combination regions. It is understood that wavelength band shifts are caused by small variations in concentration of all components in the water. Such variations, even in the range of milimoles are a common effect in the operation of the wet station. They require monitoring during an etching process together with real-time identification of similar chemical molecules and ions. Typically, an NIR spectrometer with good spectral resolution, low instrumental noise and high signal to noise ratio is suitable for the accurate and precise analytical work described herein.

An NIR spectrometer is operative to respond fast enough to fluctuations in the etch rate of an etching process. A typical response time of an NIR process spectrometer is in the range of up to several seconds while variations in the etch rate of an etching process is typically in the range of minutes. Such an NIR spectrometer used for process monitoring may be integrated or embedded into the manufacturing process as is described hereinbelow.

Many different models of spectrophotometer may be used to effect the method described in the present invention. For example, a Near Infrared Scanning Process Multiplexing Spectrometer 25 as is shown in FIG. 1, has a wavelength range 700-2500 NM. Light source 32 is a Halogen lamp, monochromator 34 is a grating monochromator and detector 62 may be an InGaAs detector. Alternately, a dual detector system may be employed. This typically comprises a silicon detector for a 700-1100 nm range and PbS detector for a 1100-2500 nm range. The scanning speed is typically less then 1.8 scans/second, and the operating range is around 3 AU. Generally, the instrumental noise is less then 0.0003 AU rms. The wavelength accuracy (SD) based on accepted wavelength standard is less then 0.30 nm. The spectral bandwidth is less than 10 nm±1 nm.

Slight changes in the concentration of bath chemicals and minor spectral differences from one bath to another may be detected by system 20 of the present invention by collecting spectra over a spectral range. System 20 may comprise standard instruments known in the art provided that they have a low noise in the range of mili absorption units and a high signal to noise ratio.

Spectral shifting may be detected in near infra-red spectra These shifts may arise for example from various changes in concentration, ionic forms of the material under study, temperature effects and flow rate of solutions. These effects may be significant and normally have to be included in a database collected and used for developing a model. System 20, comprising scanning spectrometer 25 may thus be employed to detect spectral shifting. These shifts may be very subtle to detect.

In addition there is a need for discerning minute changes in maximal values of wavelength band peaks. To be able to detect these small effects, the spectrometer has to have an extremely low background noise level in order to yield a high signal to noise ratio. This high ratio allows small differences in spectra to be detected.

Figure 3A:
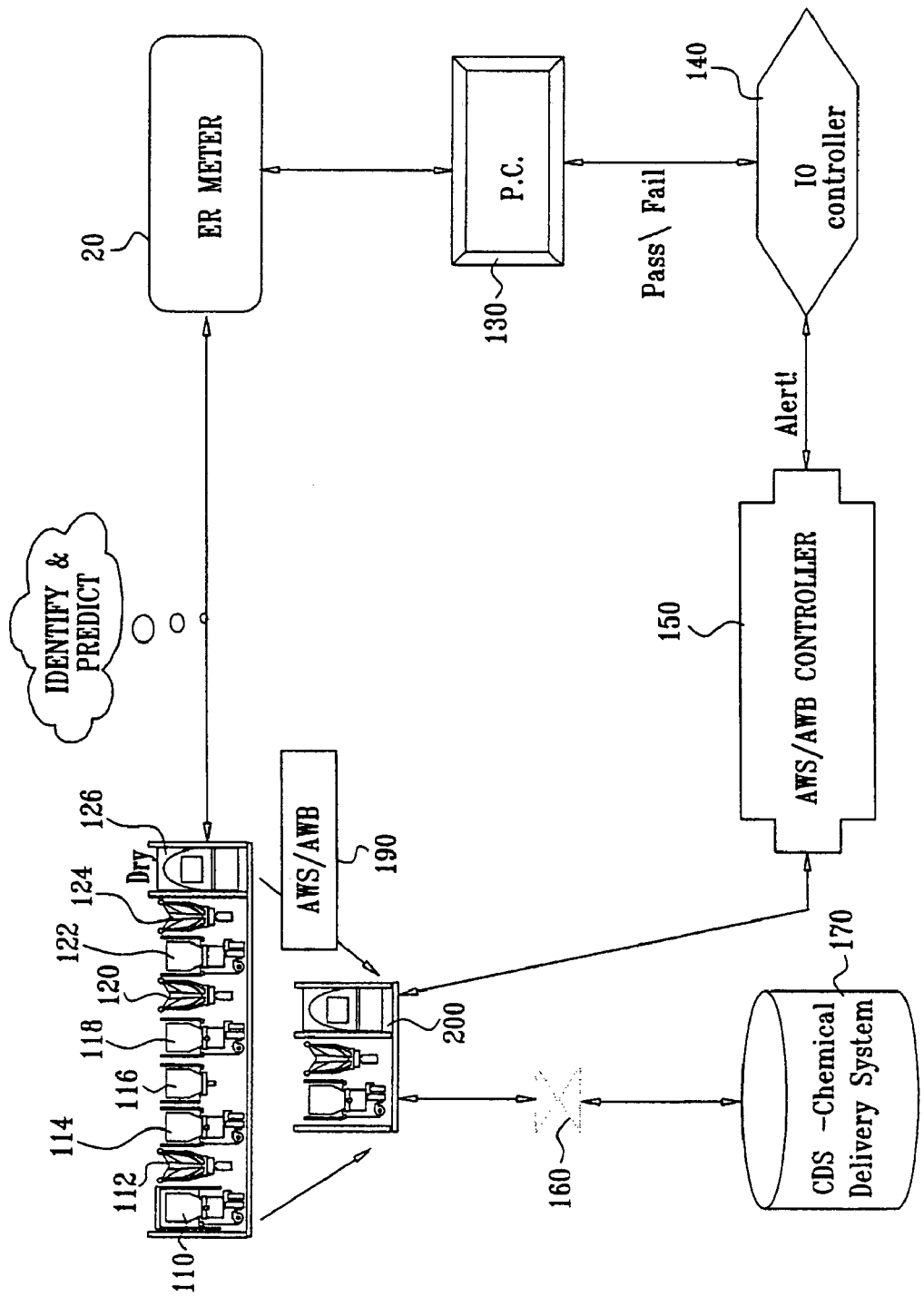
FIG. 3A is a simplified partially-schematic partially-pictorial illustration of an application of the near infra-red (NIR) measurement system of FIG. 1 as an etch rate meter in a closed loop control system of a wet station in accordance with a preferred embodiment of the present invention.

In a wet etching process one or more wafers is immersed in a tank or a bath of a liquid etching solution for a given period of time. The term "bath" is used here broadly to describe any type and size of container in which a liquid is held and/or through which the liquid is passed. Wet etching may also be performed by spraying the etching solution on the wafer surface for a specific period of time. In both cases the liquid etching solutions are circulated to achieve better contact between liquid and wafer surface and to remove etching by-products and particles adhering to wafer surface quickly. After removing the etched wafer from the bath, it is immediately rinsed with water to halt the etching process and then dried. In most cases a wet cleaning step follows the wet etching process. The wafer is treated by cleaning chemicals such as: $H_2O_2+NH_4OH$; $H_2O_2+HCl$; $H_2O_2+H_2SO_4$. Immersion in a bath or spraying in a chamber may also accomplish this. The wet processing of etching and cleaning carried out in a "automated wet station" which via robotics automatically transfers the wafers from one bath to another, immersing it for the precise period of time and maintaining the proper bath and process conditions. These conditions include temperature, chemical circulating rate and the correct sequence of drying operations. (FIG. 3A hereinbelow).

There are many types of aqueous etching solutions such as HF in various concentrations; $HF+NH_4F$; acetic acid+ $NH_4F$; $HF+HNO_3$; $HF+HNO_3$+Acetic Acid for the removal and stripping of silicon oxide and polysilicon layer, $H_3PO_4$ at an elevated temperature for the removal of silicon nitride layers, $H_3PO_4+HNO_3$+acetic acid for the removal of aluminum layers, $H_3PO_4$+chromic acid and many others. Non-aqueous etching and stripping solutions are also used such as ethylene glycol doped with 500 PPM of gaseous HF.

Each of these liquid etching solutions have different etching rates that are usually measured in angstrom per second or angstrom per minute. The desired etching depth in the wafer surface is reached by multiplying a given etch rate (ER) by the immersion time of the wafer in the bath. The etch rate values of a given bath under fixed conditions is one of the most important parameters in the wet etching process. Each time a fresh etching bath is prepared the etch rate is determined by the immersion of a "Test-Wafer" for a fixed period of time and measuring its film thickness before and after etching and then calculating the etch rate for this particular bath.

The Etching Reaction Mechanism

The wet etching of wafers with a solution of chemicals is a two phases solid/liquid heterogeneous chemical reaction type. The whole wet etching procedure may be broken into the following elementary steps (ref 3):

1) Diffusion of the etching chemicals from the bulk solution to the surface of the wafer;

2) Adsorption of reactants at the surface;

3) Chemical etching reaction on the wafer surface coated with a thin film layer;

4) Desorption of etching products and by products from the surface; and

5) Diffusion of the etching products and by products away from the surface into the bulk solution.

These are consecutive steps and if one is significantly slower then all the others, it becomes the etch rate determining step.

Steps (1) and (5) are usually rapid. Steps (2) and (4) are generally more rapid then step (3) but some chemical species tend to have slow desorption rate. Usually, however, step (3) is the etch rate determining step. It should be noted that in some cases instead of the desired etching reaction entirely on the wafer surface, molecules from the liquid phase react with the by products and with the adsorbed species.

Hydrofluoric acid (HF) is the most abundant etching chemical for $SiO_2$ layers.

In wet processing HF dissociates in water and two equilibria have been generally accepted (refs. 1 & 2):

$$HF=[H^+]+[F^-] \qquad 1,$$

$$HF+[F^-]=[HF_2^-] \qquad 2,$$

Both species HF and $HF_2^-$ etch $SiO_2$, but the etch rate of $HF_2^-$ is about 4 to 5 times greater then that of HF (ref 2). In dilute HF solution, $HF_2^-$ is much stable then HF and the ratio $[HF]/[HF_2^-]$ depends heavily on the pH and ionic strength.

The overall chemical reaction involved in the wet etching process of $SiO_2$ is normally understood as $$SiO_2 + HF \rightarrow 2H^+ + SiF_6^= + 2H_2O$$

Or $$SiO_2 + 4HF \rightarrow SiF_4 + 2H_2O$$

$SiF_4$ dissociates in water to give Fluorosilicic acid $H_2SiF_6$.

Similar chemical reactions may be set up for the etching of $SiO_2$ with $HF^{2-}$.

Fluorosilicic acid $H_2SiF_6$ together with other acids, with the general chemical formula $Si_iF_j(OH_2)_k$ where i+j+k=6 are the main by products of the $SiO_2$ etching process. It has been found that the etch rate of these chemical species is about 20 times higher than that of HF. Hence, etch rate in an aged HF bath which has been used to process many silicon wafers is higher then in a freshly prepared bath. The total etch rate in an aged HF bath is a function of the chemical etching species—HF, $HF_2^-$ and Fluorosilicic acids, each one with a different etching rate. Another conclusion is that during the life time of an HF etching bath it is impossible directly to correlate etch rate with acidity measurement of $[H^+]$ or $[F^-]$ only.

In general, it is normally understood that diffusion and migration of chemical species in the boundary layer next to the solid surface—steps (1) and (5) in the above mentioned heterogeneous reaction mechanism—and also surface absorption and desorption steps (2) & (4) are faster then the chemical reaction by itself. These steps are usually described as "boundary layer" or "diffusion layer" phenomena. They are governed by all chemical species present in the etching liquid media, the wafer surface properties and the engineering of the etching bath. The migration rate of the etching species are determined by the concentration gradient along the diffusion layer, the thickness of the this layer, its hydrodynamic properties and electrostatic charged particles and ions present (ref. 3). Wet etching system—immersion baths or spraying chambers—are engineered to control the boundary layers phenomena and to reduce its effects on the over all etching rate. Different agitation devices such as stirrers or ultrasonic and megasonic waves are added to the wet etching tools. Also different pumps re circulating the liquid etching solution are used.

Reference is now made to FIG. 2, which is a simplified pictorial illustration showing further details of a sample tube and a pair of probes in the NIR measurement system 20 of FIG. 1.

Typically, a fiber optic probe 40 is used to illuminate and to carry the energy to sample channel 42. Another fiber optic probe 44 is used for collection of energy from sample channel 42 to the spectrometer. Generally, the fibers are 1 mm anhydrous quartz fibers with a standard length of 6 m. The probe dimensions employed here are 2" length and a 1" diameter. They are made of stainless steel with a sapphire window at the tip.

A pair of probes, 40, 42 and their fiber optics are attached externally to the walls of a Teflon tube 43 containing circulating solutions the of the appropriate wet station bath (FIG. 2). This Teflon tube is part of the tubing system carrying the re-circulated chemicals from a bath, such as an etching bath, typically through a filtering system (not shown) back to the bath. There is no need to add any special sampling tubes to the wet stations.

One probe 40 carries the energy from the spectrometer to the Teflon tube. The energy interacts with the solution in Teflon tube 43. The second probe 42 collects and returns the energy to the detector 60 of spectrophotometer 25. (Hardware Installation of the fiber optics requires only two 1" holes drilled in the rear cabinet of the station.)

Tube 43 and probe 40, 42 holders 45 have been developed to hold the probes and tube in a rigid and fixed geometry without squeezing the tube. Holder 45 maintains the optical measurement parameters constant, and allows for accurate and reproducible results. These parameters include optical pathlength, spacing of the probe to the tube and minimal stray light. Tube 43 circulating the etching bath liquid is made of Teflon but any other NIR transparent material such as polyethylene, polypropylene, glass and quartz may also be used for monitoring solutions.

Reference is now made to FIG. 3A, which is a simplified partially-schematic partially-pictorial illustration of an application of the near infra-red (NIR) measurement system of FIG. 1 as an etch rate meter in a closed loop control system of a wet station in accordance with a preferred embodiment of the present invention.

A typical industrial wet bath processing station 100 is shown comprising etch baths 110, 114, and rinse baths 112, 116, followed by two cleaning baths SC1, 118 and SC2, 122, and their associated respective rinse baths 120 and 124, followed by a drying stage 126. System 20, adapted to monitor etch rate (and thus labeled etch-rate (ER) meter), receives inputs from one or more of the baths. The data is stored on a computer 130 and passed to a standard digital/analog (I/O) module 140. Module 140 dynamically integrates etch rate meter 20 into the wet station control apparatus via a closed loop.

The etching and cleaning processes of station 100 are controlled via this loop to check that the correct bath chemicals are present, and are within the correct concentration control limits. This enables the station control system, known as an automated wet station controller 150 to send signals to a chemical delivery system 170 via a valve 160 so as to correct chemical concentrations, to keep the baths topped up and to send "out of specification" alarms when appropriate. Similarly an automated wet bench station controller 190 may provide signals to the chemical delivery system 170, so as to activate it and to deliver water or chemicals to the wet bench.

Software Components

Chemometric software is used for controlling the NIR spectrometer 25 of system 20 via computer 130. This software has calibration, identification and routine operation capabilities (see FIG. 4 hereinbelow).

Chemometrics extracts information from multivariate chemical, physical and performance data using of statistical and mathematical tools.

The simplest depiction of an NIR spectrum plots the absorption of a given sample vs. the wavelengths. From this data, information may be extracted. By applying various mathematical and statistical methods to the data much information may be extracted from the spectra The combination of these methods encompasses Chemometrics. These methods perform enhancing on the shape of the spectra so as to emphasize effects and concentration of the analyte and matrix properties. Typically the manipulation applied to a spectrum is taking a derivative of the spectrum. This highlights wavelength bands and the maximal absorbency at peaks which may then be identified with the parameter being investigated. The derivative spectra may be regressed and used to predict chemical and physical properties. These properties are due to the relation between spectral effects in a given spectra data set and the changes of the parameter in the analyte and matrix properties. These spectral effects include wavelength band height changes, band shifting among others.

Regression techniques used include Principal Component Analysis, Partial Least Squares, Multiple Linear Regression and Neural Network Analysis. In each technique, a model depicting the relationship between a given analyte and matrix and the spectral effects is developed. This model may then be applied to subsequent spectra being collected and the concentration analyte or other property of the analyte and matrix of the model may be predicted.

Another aspect of Chemometrics is its ability to compare a given spectra and a defined fingerprint of a specific sample set. This allows a given spectra to be identified as a given species separate from others. These same collected spectra may be qualified against the data set base pointing to even slight changes in the sample. The sample may then be rejected or further tested to investigate the cause of these changes.

In the development of the algorithm, two regression techniques were employed, namely, principal component analysis and partial least squares as are described hereinbelow.

The procedure of developing an algorithm for near infrared analysis is well defined in ASTM E1790-00 entitled "Standard Practice for Near Infrared Analysis Principal Components Analysis (PCA) regression is a multivariate data analysis technique for resolving sets of data such as NIR spectra into orthogonal components whose linear combinations approximate the original data to any desired degree of accuracy. PCA breaks apart the spectral data into the most common variations (factors, eigenvectors, loadings) and the corresponding scaling coefficients (scores).

Partial Least Squares (PLS) regression is a multivariate data analysis technique, which may be used to relate several response (Y) variables to several explanatory (X) variables. PLS may deal efficiently with data sets where there are very many variables that are highly correlated and involve substantial random noise.

An algorithm is used to predict etch rate values, chemical concentration and identification of bath content from NIR spectrum. The algorithm is created from a data set of spectra that includes spectra of bath content of varying concentrations and other effects in the bath. The other effects include aging of bath as by-product(s) of the normal processing of production wafers accumulate in the bath, different re-circulation flow rates of bath chemicals, static condition of the bath when re-circulation halts, temperature changes etc.

Etch Rate Measurement

To measure etch rate, a test wafer of known thickness is immersed in the bath for a given amount of time. This time interval is defined as the time from initial immersion of the wafer in the bath to the time the wafer is removed from the bath and immersed in a bath of DIW to stop the etching process. The wafer is then rinsed and dried. Then the wafer is re-measured to find its current thickness. The difference between the thickness pre-immersion and the thickness post-immersion is the amount of etching depth on the wafer. Dividing the amount of etching depth by the time interval yields the etch rate expressed in Angstrom/second or Angstrom/minute. The same test wafer may be re-used a number of times.

Etch Rate Spectra Database Collection.

A wide and representative database of spectra of baths of varying "age" and etch rates is required. The age is related to the number and type of wafers processed in the bath. To include in the database as wide a variation as possible, a given bath has its etch rate varied to produce spectra with the same aging effects but of varying etch rates. The etch rate is varied by increasing or decreasing the concentration of HF in the bath. This is accomplished by adding DIW to the bath to dilute the HF concentration or by adding HF of a higher concentration to increase the etch rate.

An example of the process is as follows. A bath is obtained of 1% HF in DIW (commercially known as HF 50:1). A test wafer of known thickness is passed through the bath under controlled conditions including temperature, immersion time. To facilitate the control this is done by robotics. Concurrent to the test wafer a number of spectra of the bath solution are collected by the spectrometer and stored on a computer. When the wafer has finished being processed, the post-immersion thickness is measured and the etch rate is calculated. This etch rate is connected to the spectra collected during the above process. The spectra and be averaged or used separately.

To increase the etch rate of a bath, a solution of 10% HF in DIW (commercially known as HF 5:1) concentration is added. The amount added depends on the increased etch rate required and the concentration of solution in the bath. Each increase of 0.01% of HF will theoretically cause an etch rate change of 0.01 angstroms per second.

In order to increase the etch rate to a given rate, approximate the amount of pure HF presently in the bath by multiplying the etch rate by the amount of solution and then dividing by 100. Divide the required etch rate by 100. Multiply this by the amount of solution in the bath. This yields the amount of pure HF that is needed in the bath for the required etch rate. From this amount subtract the present amount of pure HF in the bath, yielding the amount of pure HF that is to be added. Divided this amount by the concentration of the HF solution used for the addition to give the amount of concentrated HF solution to be added. The new etch rate will not be exactly the calculated one due to the increased amount of solution with the addition and other ionic effects. Once added, the bath should circulate for enough time to allow for the solution to mix properly and reach ionic equilibrium. Once this time has passed a new test wafer is run through the bath and spectra collected as above. Then the process is repeated for as many times as is required.

To decrease the etch rate of a bath, the bath is diluted by adding deionized water (DIW). The amount of DIW to be added depends n the decrease in etch rate desired. A decrease of HF concentration of 0.01% will decrease the etch rate by 0.01 Angstrom per second. To decrease the etch rate to a given rate, approximate the amount of pure HF presently in the bath by multiplying the etch rate by the amount of solution and then dividing by 100. Divide the required etch rate by 100. Multiply this by the amount of solution in the bath. This yields the amount of pure HF that is needed in the bath for the required etch rate. From the present amount of HF in the bath subtract the desired amount of pure HF in the bath, yielding the amount of pure HF that is to be removed. Divide the amount of pure HF to be removed by the present concentration of the bath to yield the amount solution to be removed and replaced by DIW. While not exact, the amount of DIW to be added may be added without removing the solution. In this case care has to be taken to prevent over filling. Once replaced, the bath should circulate for enough time to allow for the solution to mix properly and reach ionic equilibrium. Once this time has passed, a new test wafer is run through the bath and spectra collected as above. Then the process is repeated for as many times as needed.

The etch rates in the database should vary by approximately 20% above and below the target etch rate and/or 5% above the upper control limit and 5% below the lower control limit of the bath.

The database includes, but is not limited to, baths of aged solutions up to two weeks old with various type and amounts of process wafers.

The database should include flow rate effects by collected spectral and etch rate data with varying pump flow rates. This also includes spectra collected in a static state when there is no mixing or re circulation of chemicals.

The database should include etch rates of a given bath at varying temperatures.

Single Chemical Concentration Data Base

Concentrations of a bath are measured by sampling the bath and placing the sample in an appropriate holder. The sample is then analyzed by appropriate chemical analytical methods known in the art. Proximate to the sampling, spectra of the solution are collected and the concentrations found by laboratory analysis are compared with the spectra. The concentrations of a given bath are varied by adding the given solution to the bath or diluting by adding DIW to the bath.

The concentrations in the database should vary by approximately 20% above and below the target etch rate and/or 5% above the upper control limit and 5% below the lower control limit of the bath.

The database includes, but is not limited to, baths of aged solutions, which are kept active up to reaching the replacement criteria, and includes baths with various type and quantities of process wafers.

The database also includes flow rate effects by collecting spectra of a given concentration of an acid or chemical with varying pump flow rates.

The database also includes spectra and concentrations of a given bath at varying temperatures.

Figure 3B:
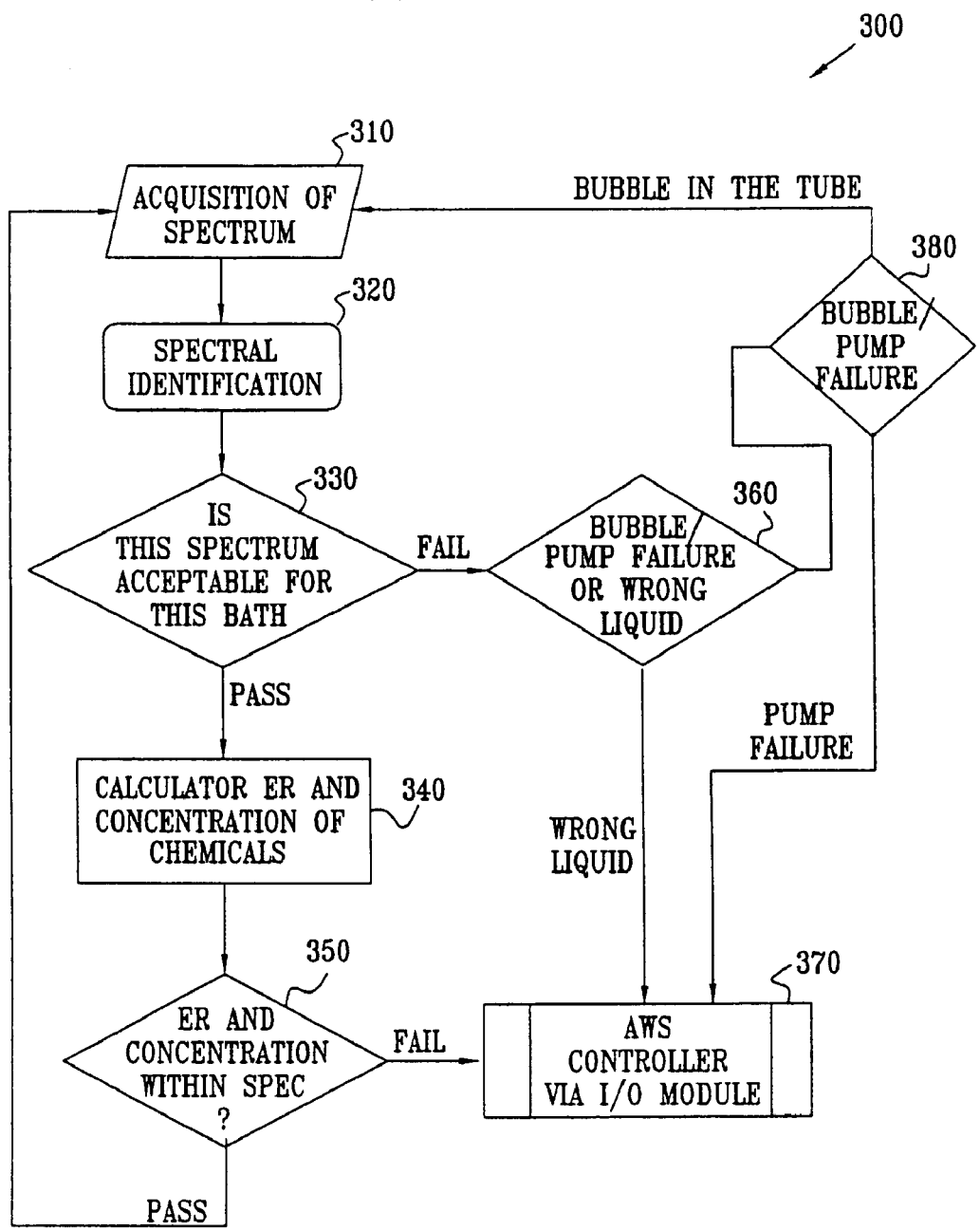
FIG. 3B is a simplified flowchart of a real-time method of analysis of an etch rate of a substance based upon the concentration of chemical sample in accordance with a preferred embodiment of the present invention.

Reference is now made to FIG. 3B, which is a simplified flowchart of a real-time method 300 of analysis of an etch rate of a substance based upon the concentration of chemical sample in accordance with a preferred embodiment of the present invention.

In an acquisition step 310, a spectrum of a single or multiple component is acquired employing the NIR spectrophotometer 25 of FIG. 1.

For building a multi-component chemical concentration database, concentrations of a bath, such as bath 114 of FIG. 3A, are measured by sampling the bath and placing the sample in an appropriate holder, such as sample tube 43 in FIG. 2. The sample is also analyzed by appropriate chemical analytical methods known in the art. A large number of samples are analyzed both chemically and spectrally, and relevant correlations an their confidence levels are determined.

In an identifying step 320, a new spectrum is compared with those in a database and is identified as belonging to a specific chemical component. Data is fed into computer 130 (FIG. 3A), for example to provide standard spectra of components, as well as their boundary limits and set points of each of a multiple of components for each of the baths in the wet station. In a decision stage 330, computer 130 checks whether the spectral identification is within the acceptable set of one or more components of the bath, received from spectrophotometer 25. If the spectrum is positively identified, computer 130 (FIG. 3A) or processor 64 (FIG. 1) accepts the spectrum as having been positively identified. The acceptance indication is passed onto a calculation stage 340, in which the computer or processor performs calculations of concentrations and etch rates of the solids as a function of the spectral data received from spectrophotometer 25.

If the spectrum is not positively identified in stage 330, computer 130 passes the information onto a negative indication stage 360. Typically at stage 360, the computer identifies whether the spectrum belongs to another known chemical, to a bubble or to a pump failure. If the chemical is not known, the computer passes this information to the AWS controller 150 (FIG. 3A). If another fault selected from a bubble or pump failure is detected, the computer passes this information to a system circulation analysis step 380. In step 380, it is discerned whether the fault is a bubble or a pump failure, based upon a spectrum identification algorithm. Step 380 outputs a result which defines whether the fault was a bubble or pump failure. In the case of a bubble, step 380 relays an instruction to repeat acquisition step 310. In the case of a pump failure, step 380 inputs this information to the AWS controller 150, which typically activates an alert [FIG. 3A].

In a concentration acceptance stage 350, the computer checks if the concentration and/or etch rate of the bath received from stage 330 falls within its acceptable control/statistical limits. If the concentration/etch rate is in the acceptable range, then system 20 (FIG. 1) is ready to take another reading of the spectrum/spectra or to proceed to measure parameters of another bath. If the results are within control limits, the AWS proceeds and the meter 20 moves on to the next bath to be monitored. Data may be sent to the data collection system and the processed wafer history may be updated by computer 130 with the data collected when the wafer was processed in a bath.

Topping: When the liquid level of a bath drops below a given height, additions must be made to raise the level of liquid in the bath. Employing the closed loop system described in FIG. 3B, this addition is optimized by the addition of the correct acid and/or water as is required, and as is dependant on the ER or concentration last reported by the monitor (FIGS. 10 & 11).

If the ER/concentration is not within the accepted range, then the computer passes a signal to AWS controller 150.

Spectral Identification: If the wrong chemicals have been added or other serious mis-processing occurs, stage 330 sends a failure message and an alert is sent to the AWS controller 150 and the bath function is stopped until corrective steps have been taken.

In a multiple component bath system, a matrix of theoretical concentrations is developed. The number of dimensions in the matrix is equal to the number of components tested in the bath. Each dimension represents one component. The concentrations in each dimension are to vary by 5% above and below the maximum and minimum concentrations as defined by the control limits of the bath. At least 30 to 50% of the boxes of the matrix concentrations are collected spectrally and sampled for chemical analysis.

The concentrations of a given bath are varied by adding the given solution to the bath or diluting by adding DIW to the bath.

The concentrations in the database should vary by approximately 20% above and below the target etch rate and/or 5% above the upper control limit and 5% below the lower control limit of the bath.

The database includes, but is not limited to, spectral data from baths of aged solutions up the replacement criteria employed by the user and should include baths with various types and quantities of process wafers.

The database typically includes data concerning flow rate effects, collected by measuring spectral changes of a given concentration of acid, while with varying pump flow rates. This include also spectra collected in a static state when there is no mixing or re circulation of chemicals.

The database should include spectra and concentrations of a given bath at varying temperatures.

Prediction Model Creation

To create a model for predicting etch rates and/or chemical concentrations, various chemometric methods and manipulations are applied to the data. These methods include pre-data treatments such as detrend, multiplicative and taking the derivative of nth order of the spectra. Approximately 15% of the spectra in the database are set aside to function as a validation of the various models created.

Then using PLS, the database is analyzed to create a modeling relationship between the spectra and a component associated with the spectra Varying the parameters of the used by PLS creates various models. These parameters include using various pre-treatments alone and in combination and the number of factors used in the model.

This model is tested using the spectra from the database set aside and by real time data collected during wafer processing. For each model tested the Standard error of the model, the Standard error of the validation sets, and the R2 are recorded. The top models are identified and then tested in real time to choose the model that best predicts the component in question.

Spectral Identification and Qualification.

Spectral identification functions to identify the type of chemical in a given solution and to eliminate the identification as another chemical. To accomplish this databases that will be used on a given machine are combined into a new database. Each previous database is now a separate product within the combined database. Using Chemometric procedures a model that will positively identify each product and not falsely identify the product is developed. To accomplish this various pre-data treatments are applied separately and in combination. Using various methods including spectral correlation, Maximum spectral distance, Mahalanobis distance and residual in principal component space. Each method is tested using the validation sets and the best method is identified.

Qualification of spectra applies the same methodology as identification but only on a given product. The parameters of qualification are tighter. This creates a model that will identify slight changes in a new spectrum and will warn of the change.

Operation Method

An operation method consists of an identification method consisting of the products that will be tested by the unit at a given site, a qualification method that will test that the given spectrum is within the parameters set by the qualification model and a predication model for each component of each product. This is then outputted to a screen and or a controller and or a data collection system.

Additional software based on the SECS protocol has been developed for interfacing the process spectrometer operational software, data collection system, and the AWS controller. The closed loop schematics are shown in FIG. 3 hereinabove.

Figure 4:
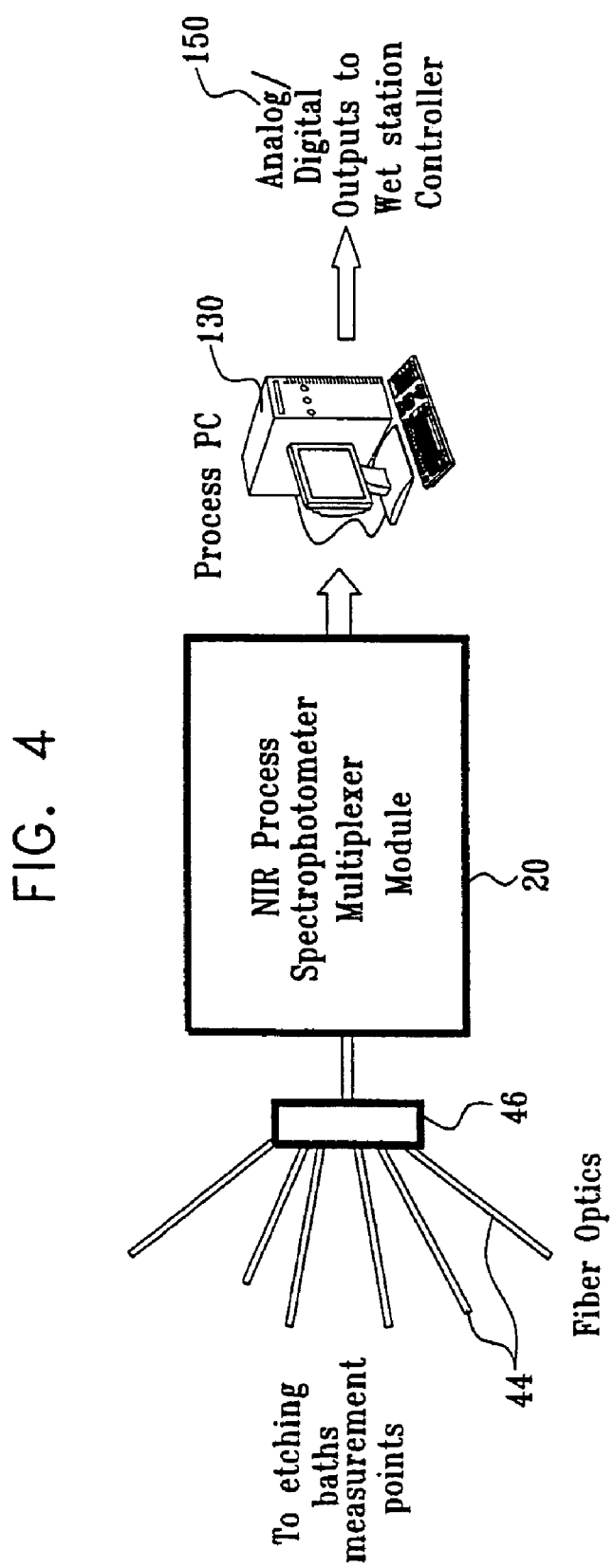
FIG. 4 is a simplified partially-schematic partially-pictorial illustration of a near infra-red (NIR) measurement system of FIG. 1 applied to control multiple points of a wet station in accordance with a preferred embodiment of the present invention.

Reference is now made to FIG. 4, which is a simplified partially-schematic partially-pictorial illustration of a near infra-red (NIR) measurement system of FIG. 1 applied to control multiple points of a wet station in accordance with a preferred embodiment of the present invention. Typically, optical probes 44 from wet station baths lead to multiplexer 46 (as is shown in FIG. 1). System 20 analyzes the optical inputs from multiplexer 46, and provides data to computer 130. Wet station controller 150 receives inputs from computer 130, and activates controls and chemical delivery system 170.

Modeling: Calibration & Validation

HF Etching Baths

Figure 5:
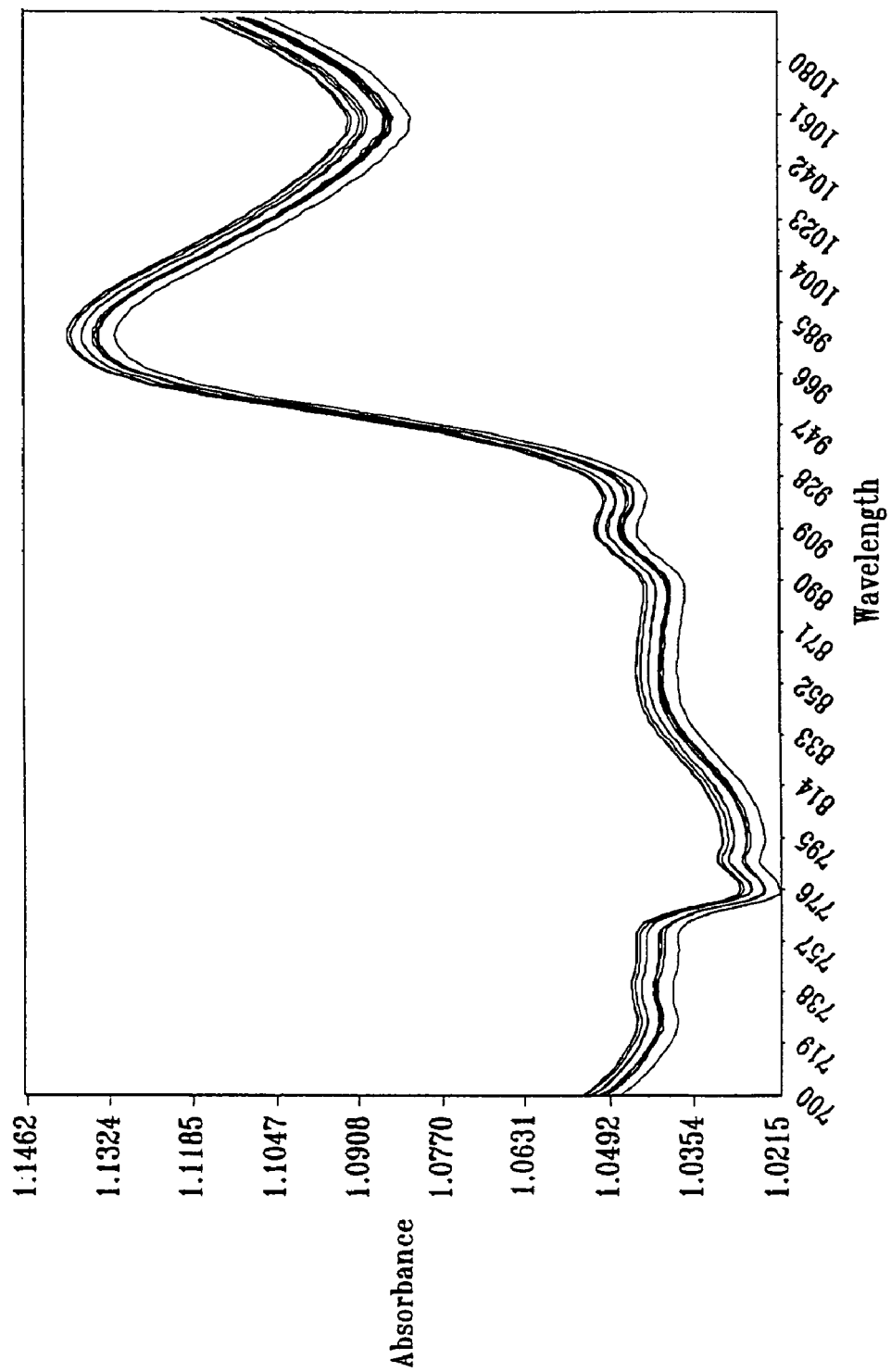
FIG. 5 is a series of measurements of a spectrum in the near infrared range of 50:1 hydrofluoric acid.

Reference is now made to FIG. 5, which is a series of measurements of a spectrum in the near infrared range of 50:1 hydrofluoric acid. Spectra of bath etching chemicals were recorded on-line with the etch-rate meter 20. FIG. 5 shows several spectra of slightly different HF concentrations and Etch Rates (ER). The differences between concentrations are reflected in baseline shift and absorbance intensities.

Figure 6:
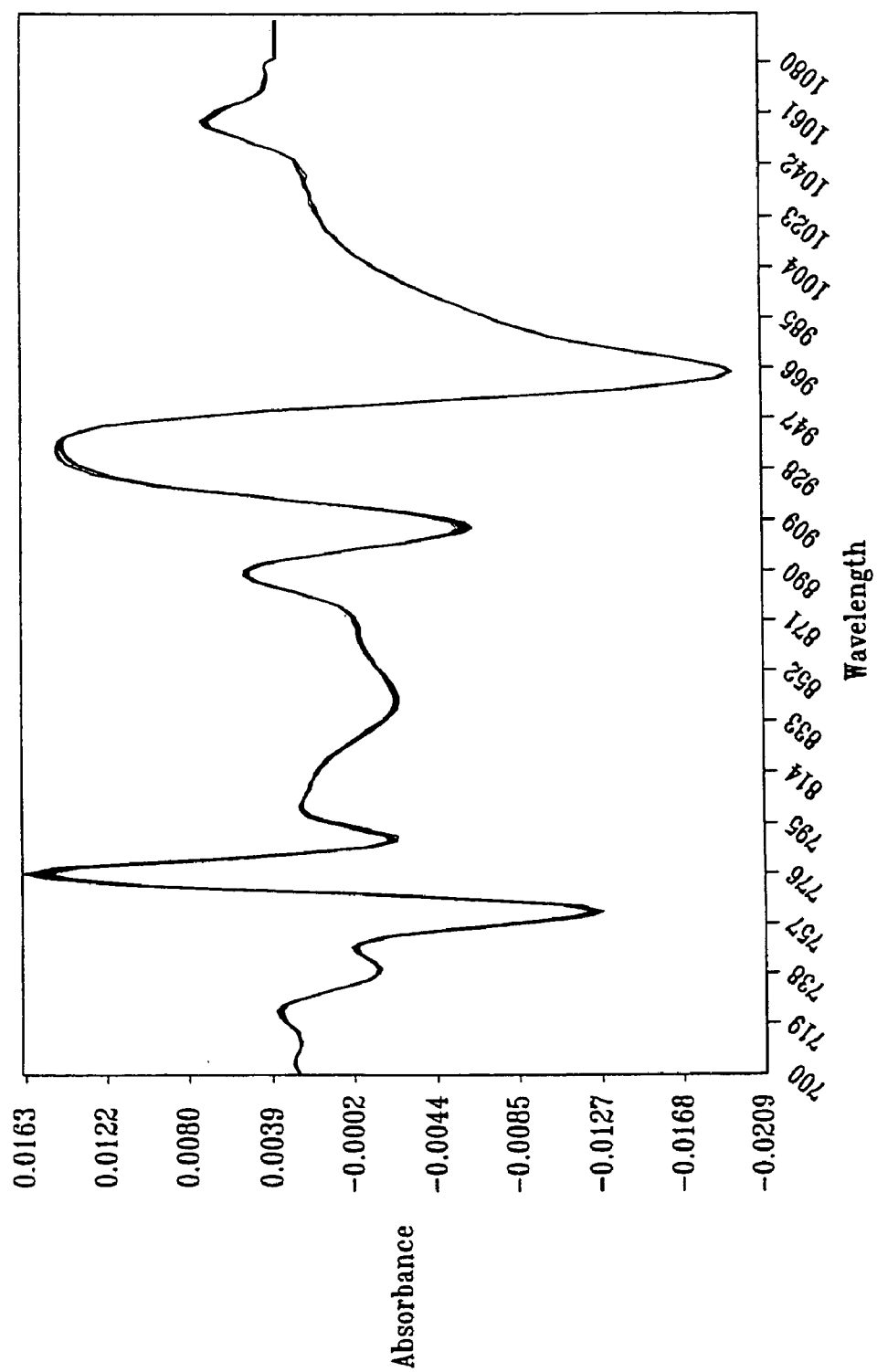
FIG. 6 is a second derivative of a spectrum in the near infrared range of 50:1 hydrofluoric acid of FIG. 5 in accordance with a preferred embodiment of the present invention.

Reference is now made to FIG. 6, which is a second derivative of a spectrum in the near infrared range of 50:1 hydrofluoric acid of FIG. 5 in accordance with a preferred embodiment of the present invention.

The second derivative of the spectra is used for the chemometric modeling (FIG. 6). The chemometric model was based on approximately 140 samples of HF baths with different ER values and operational conditions.

To create a precise, accurate and robust calibration, model spectra of real working conditions are included in the model training set. The model includes ER values of a fresh prepared bath, an aged bath (up to 9 days) containing various etching by-products, diluted etching solutions, dynamic baths with different flow rates, steady-state baths without. circulation, bubbling in the baths and in the Teflon tubes circulating the bath chemicals.

The model is created using a PLS (Partial Least Square) algorithm. The database spectra recorded on-line and their corresponding test wafer ER are regressed against each other in a multi dimensional space. A model using Partial Least Squares was created to predict ER from spectra.

Figure 7:
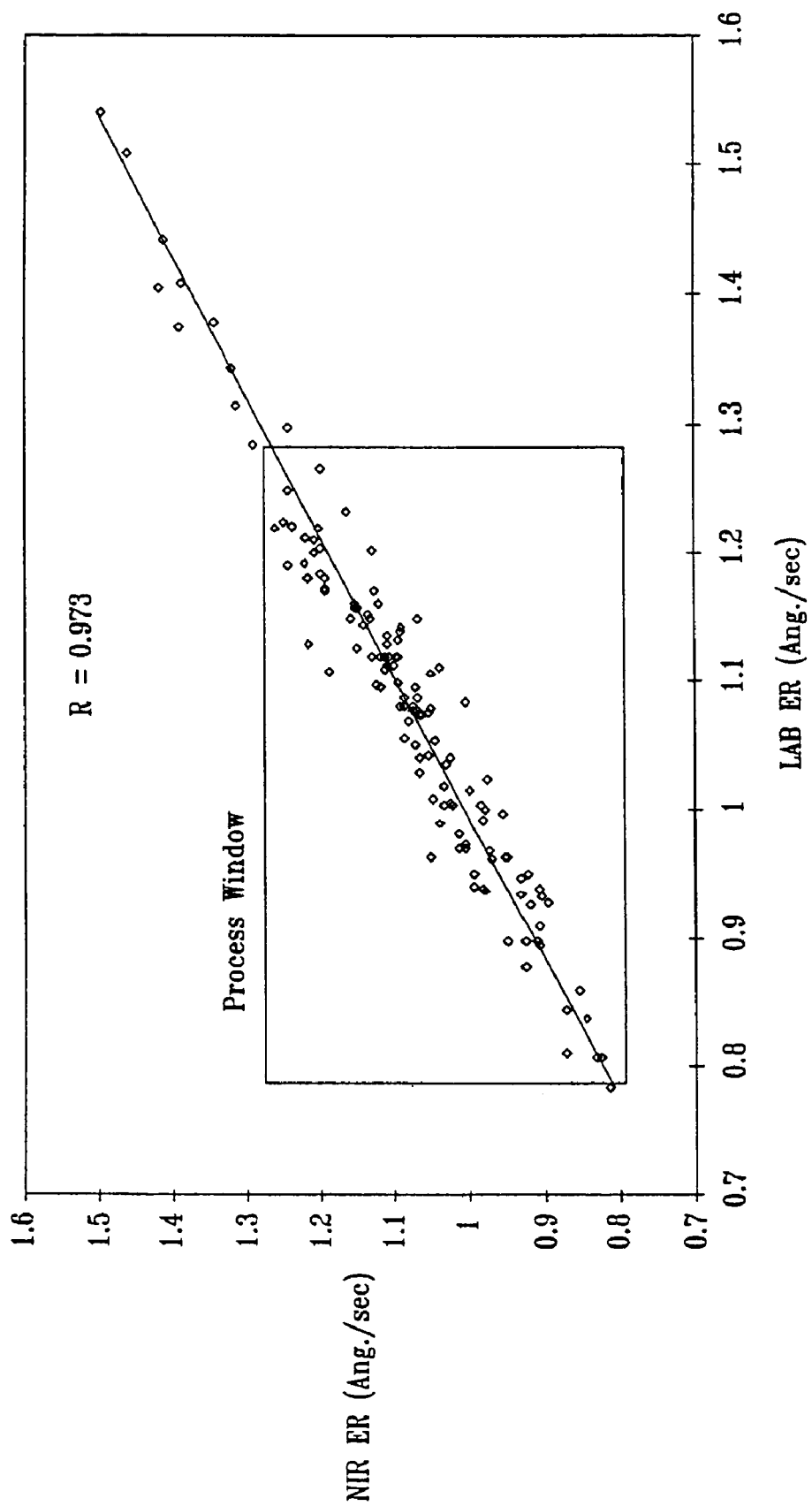
FIG. 7 is a calibration curve of the etch rate of silicon dioxide by hydrofluoric HF 50:1 measured by an etch rate meter, in accordance with a preferred embodiment of the present invention.

Reference is now made to FIG. 7, which is a calibration curve of the etch rate of silicon dioxide by hydrofluoric HF 50:1 measured by etch rate meter 20, in accordance with a preferred embodiment of the present invention. The calibration correlation (FIG. 7) shows a very good correlation of R>0.97.

Furthermore, a validation set of 25 test wafers (TW) was also created and gave similar results, as is shown in Table 1 hereinbelow.

TABLE 1

| HF bath conc. | No o samples Cal./Val | ER range Angs/sec | R calibration | Standard Error calibration | R validation | Standard Error validation |
|---|---|---|---|---|---|---|
| 1:50 | 140/32 | 0.8-1.35 | >0.96 | 0.04 | 0.93 | 0.05 |
| 1:5 | 130/28 | 8-12.5 | >0.97 | 0.25 | 0.95 | 0.35 |

Test wafers used for the off line etch rate measurement were 6"in diameter with a homogenous 6000-angstrom silicon oxide layer. Thickness of layer—pre and post etching —was measured with a FT layer thickness-measuring tool, for example, and several points were averaged, and the ER was calculated accordingly.

All etch rate meter development was performed on a wet processing production line tool located in a wafer production site. This allowed for collection of spectra of actual process conditions and problems. The Automatic Wet Station (AWS) was a commercial type with HF etching bath, SC1 and SC2 cleaning baths, DI $H_2O$ quick rinse and dump bath and wafer spin-rinse dryer (FIG. 3A). The automated wet station was operated by robot via a control system. All chemicals and DI $H_2O$ used were microelectronics grade.

Figure 8:
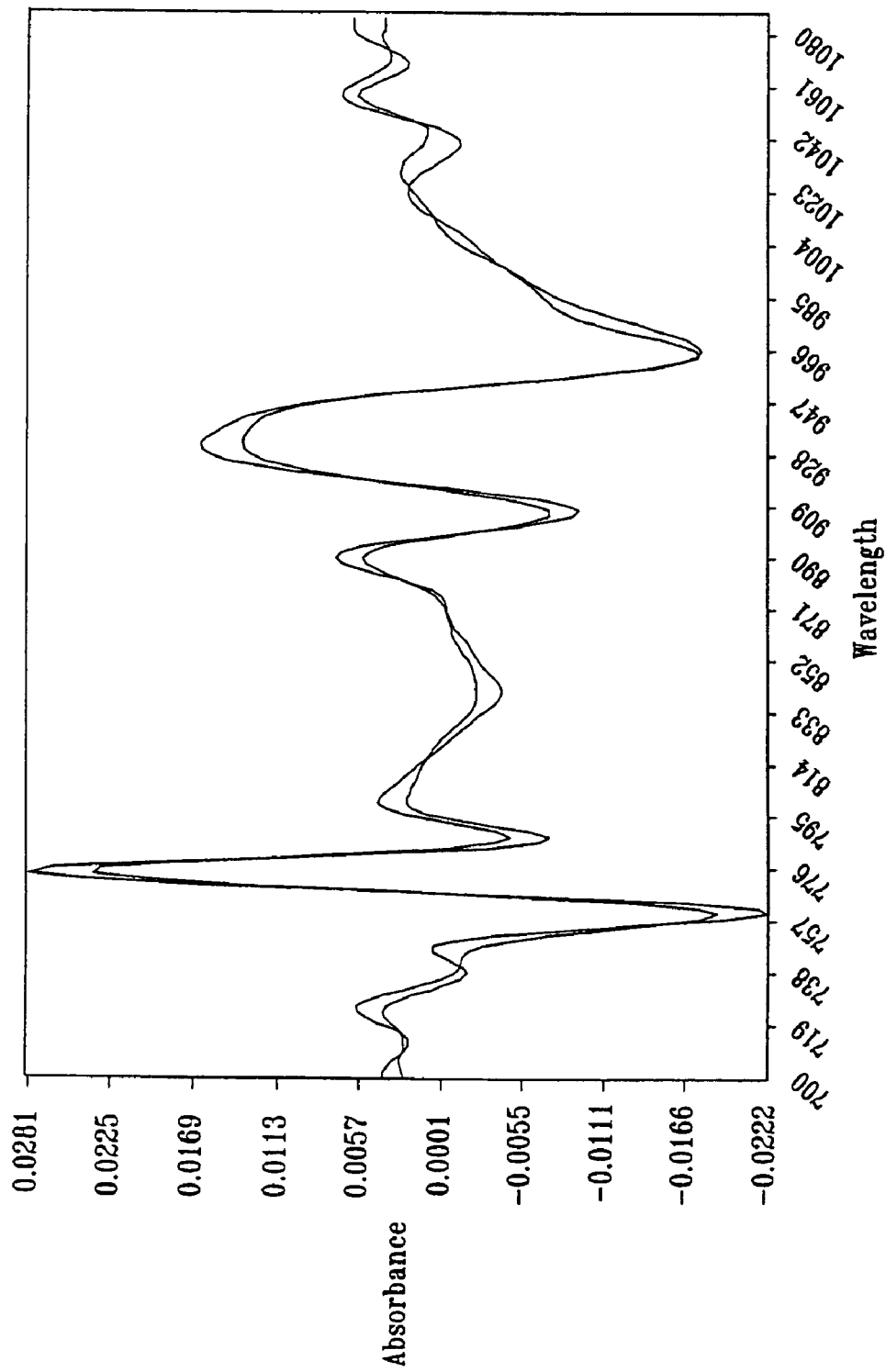
FIG. 8 is a graph of a second derivative of a spectrum in the near infrared range of 50:1 hydrofluoric acid of FIG. 5 and of 5:1 1 hydrofluoric acid in accordance with a preferred embodiment of the present invention.

Reference is now made to FIG. 8, which is a graph of a second derivative of a spectrum in the near infrared range of 50:1 hydrofluoric acid of FIG. 5, and of 5:1 1 hydrofluoric acid in accordance with a preferred embodiment of the present invention. For the development of NIR Spectral identification library, spectra of the different bath compositions were recorded. FIG. 8 shows the differences between similar acids but of significantly different chemical concentration. Each composition or bath formula has its own spectral pattern "fingerprint". An PCA exploratory algorithm was designed to reduce large complex data set (of multi components bath) into a set of interpretable values. Using these spectral fingerprints and well-defined spectral parameters baths may be identified and qualified.

Identification of bath chemical composition is the key to 100% elimination of process deviations. There are many cases where wafers are etched or cleaned with the wrong chemicals causing the scrapping of hundreds processed wafers. The current TW batch monitoring method typically practiced on most AWS systems does not give real time solution to the this problem.

RCA Cleaning Baths

In modeling SC1 and SC2 cleaning baths, similar methodology was used as described above. The bath spectra were recorded on line by the etch rate meter and chemical concentrations were determined off line with classical analytical methods These were regressed against each other to create the concentration algorithms.

Reference is now made to FIG. 9, which is a calibration curve of the concentration by hydrogen peroxide in bath SC1 (FIG. 3A) measured by etch-rate meter 20, in accordance with a preferred embodiment of the present invention. An excellent correlation—R>0.98, and relative Standard Error of less then 5% were calculated for $H_2O_2$ and $NH_4OH$ in SC1 and $H_2O_2$ and HCl for SC2.

Samples in the training set for SC1 and SC2 chemometric modeling included samples from baths in the production line processing wafers. The set includes samples from fresh baths, used baths processing different types of wafers, aged baths up to 24 hours, diluted solutions and baths with different flow rates. As in the HF sets, the training set represent real bath conditions to create an accurate, precise and robust calibration model. This is of crucial importance in calibration development for a bath with relatively fast depletion chemicals such as $H_2O_2$, $NH_4OH$, $DIO_3$ etc.

Reference is now made to FIG. 10, which is a graph showing the effect of a water addition on the etch rate measured by an etch-rate meter, in accordance with a preferred embodiment of the present invention. Furthermore, FIG. 11 is a graph showing the effect of a hydrofluoric acid addition on the etch rate measured by an etch-rate meter, in accordance with a preferred embodiment of the present invention.

AWS Moitoring

The etch rate meter 20 is interfaced with the AWS controller 190 via the I/O controller module 140 as described in FIG. 3B. As was described in FIG. 3B, after the spectra have passed the first stage the ER or concentrations of the bath components are calculated based on developed algorithms. If the results are out of the control limits the bath is stopped and correction steps are taken by the operator or automatically by the AWS control apparatus. A given component of the bath is added to bring the results back into specifications. For example when high ER values are reported water is added (FIG. 10), and when low ER is reported the appropriate acid is added (FIG. 11).

Reference is now made to FIG. 12, which is a graph displaying a correlation of the effect of temperature on an etch rate measured by an etch-rate meter, in accordance with a preferred embodiment of the present invention. ER values may be corrected according to the temperature correlation (as is shown in FIG. 12).

FIG. 13 is a graph displaying a correlation of the effect of stopping a circulating pump of a process bath on an etch rate as a function of time measured by an etch-rate meter, in accordance with a preferred embodiment of the present invention. Thus, pump stoppage may be detected using ER meter 20, and an appropriate action may be taken. This is shown by constant ER values (FIG. 13) without a typical saw tooth profile.

FIG. 14 is a graph displaying a correlation of the effect of bubbles in the sample tube as a function of time on an etch rate measured by an etch-rate meter, in accordance with a preferred embodiment of the present invention. Bubbles in a sampling tube 43 or bath 114, for example, may be detected and appropriate action taken. Bubbling effects have a typical profile, as exemplified in FIG. 14.

Reference is now made to FIG. 15, which is a simplified time chart of measurements of etch rate made by an etch meter compared to those made with test wafers, in accordance with a preferred embodiment of the present invention. Typically, the etching bath composition changes over time. These changes significantly effect the etching properties of the etching bath and its ER. FIG. 15 is a time chart of a 1:5 HF etching bath over nine days. This time chart is from an on-line, continuous record of ER reported by the Etch Rate Meter. The increasing ER trend may be seen clearly from both ER meter 20 measurements and from test wafer measurements.

There are two main reasons for the increase in the ER during the lifetime of an etching bath:

A) Evaporation of one or more components. For example water evaporation increases the concentration of the active etching chemicals leading to an increase of the etch-rate.

B) During the etching process by-products such as fluorosilicic acids are formed by the etching of the silicon oxide layer by HF. These by-products are stronger enchants then the HF by itself (ref. 4)

The instability of the bath composition may also be caused by drag out of liquid when removing the wafer lots out of the bath. This and simple evaporation cause low liquid level in the bath. When this occurs the AWS controller 150 (FIG. 3A) stops processing wafers and waits for topping the bath liquid to return the solution to the right height. Usually the ER changes before and after the topping requiring testing the ER of the bath with a test wafer. This topping process is a source of many error and process deviations.

Examples from the time chart on FIG. 15 may be seen. At midday on day 4 topping of the bath was done with HF, increasing the ER (ER operating window is 8.5 to 11.5 Angstrom /sec). On days 5 and 9 the bath was topped with water. On day 7 the bath acids were replaced.

ER is typically tested every 8 to 12 hours, and when bath conditions change due to topping, chemicals change, temperature, flow rate, any maintenance work etc The ER measurement by a test wafer is a time consuming procedure. Work on the bath has to be stopped, a TW run and then film thickness measurements—pre and post immersion—done off-site and manually. The 45 to 90 minutes spent during this measurement procedure causes a significant decrease in the wafer throughput of the wet station. In effect this is a batch type measurement of the ER of the wafers that ran through the wet station over the time period between the ER measurements. This mode of operation makes the implementation of on-line real time wet etching process control—as is practiced in many other wafer-processing tools—impossible.

The large quantities of test wafers that are required for process control of the prior art are expensive. The downtime during ER measurement reduces processing up-time, increases labor and costs and reduce wet station capacity. The infrequent nature of TW etch rate measurement complicates the use of the etch rate data, and may not give a true real-time "picture" in case of process deviations or any other mis-processing. Traditional prior art ER testing does not permit any real time adjustment of chemical concentration to optimize the process conditions, or for correlating process characteristics to end of line quality control data.

Circulation rates of the etching and cleaning chemicals are very important to achieve better contact between the etching chemicals and the wafer surface. The circulating rate depends on pump discharge rate, piping and valves and spray nozzles when using spray chambers. Small changes in this dynamic system lead to significant changes in the ER. Bubbles created in the bath liquid due to pump and mixing failures may greatly disturb the etching process.

Reference is now made to FIGS. 16A and 16B, which are simplified charts displaying a concentration of two components in a SC1 and SC2 process bath measured by an etch meter, in accordance with a preferred embodiment of the present invention.

The etch rate meter of the present invention simultaneously measures ER and concentration of chemicals. Unstable cleaning baths such as SC1, SC2, $H_2SO_4/H_2O_2$ contains chemicals that deplete rapidly over time. ER meter 20 follows concentration changes of each component over time.

The time chart for SC1, FIG. 16A, shows that $NH_4OH$ depletes faster then $H_2O_2$ while the time chart for SC2, FIG. 16B, shows that both components $H_2O_2$ and HCl have approximately the same decomposition rate.

Reference is now made to FIG. 17, which is a simplified flowchart for the methodology of development of the chemometric-based algorithm according to a preferred embodiment of the present invention. In a developing training stage 400, a set of data is produced from spectral measurements as described hereinabove. Thereafter, in an application stage 410, standard commercialized software is applied to the training set of step 400. Examples of the software include, but are not limited to Vision™ produced by Foss-NIRSystem Inc. (Maryland, US).

In a producing stage 420, a resulting algorithm is produced which can be applied to further samples to determine at least one of an etch rate and a concentration of a chemical in a liquid phase.

List of Abbreviations:
AWS—Advanced (Automated) Wet Station
CDS—Chemicals Delivery System
DIO3—Ozonated (O3) Distilled Water
DIW—De Ionized Water
ER—Etch Rate
NIR—Near Infra Red
NIRA—Near Infra Red Analysis
PE—Polyethylene
PCA—Principal Components Analysis
PLS—Partial Least Square
PP—Polypropylene
RCA—Wafer cleaning methods developed by Radio Corp. of America
SC1—Standard Cleaning method #1
SC2—Standard Cleaning method #2
SECS—Semiconductors Standard Software
SPC—Statistical Process Control
TW—Test Wafer The following references are incorporated herein by reference:

1. Wet chemical processing: HF etching
   De Keersmacker, R., (Editor) Dielectric Breakdown in Thermally Growing Oxide Layer—Chap. 7, Katolieke Umiversitett Leuven, Belgium, 1993
2. A Study of the Dissolution of SiO2 in Acidic Flouride Solutions
   Judge, J. S., J. Electrochem. Soc. (1971) November p. 1772-5
3. Physical Chemistry
   Moore, Walter, J. $4^{th}$ Edition, Longmans
4. Using UV absorption and other methods for monitoring wet process
   Carpio, R. A., et al.
   Electrochemical Soc. Proc. 1994, Section Vol.: Contamination Control and Defect Reduction in Semiconductors Manufacturing III
5. Handbook of Near Infrared Analysis
   Ciurzcak and Burns (Editors ) Marcel Dekker Inc. 1992
6. HF Concentration Control in IC Manufacturing
   Kashkoush,I. et al., Mat. Res. Soc. Symp. Proc. (1997) 477 p. 311
7. Correction to the Baseline Distortion in the OH-Stretch Region of Aqueous Solutions Fischer, Wolfgang, B. et al. Appl. Spec. 1994, 48, (1) p. 107-112
8. Quantification of HF Species by Chemical Regression Modeling of NIR Spectra
   Thompson C. J., Anal Chem. 1997, 69, p. 25-35

List of Relevant U.S. Patents:
1. U.S. Pat. No. 5,893,046 (1999) Wu, et al. Real time monitor of reacting chemicals in semiconductors manufacturing.
2. U.S. Pat. No. 5,938,885 (1999); U.S. Pat. No. 5,830,375 (1998) Huang et al. Automated method for monitoring and controlling the orthophosphoric acid etch rate of silicon nitride insulator layers
3. U.S. Pat. No. 5,788,801 (1998); U.S. Pat. No. 5,582,746 (1996); U.S. Pat. No. 5,500,073 (1996); Barbee, et al. Real time measurement of etch rate during chemical etching process
4. U.S. Pat. No. 5,694,207 (1997) Huang, et al. Etch rate monitoring by optical emission monitoring.
5. U.S. Pat. No. 5,573,624 (1996) Barbee, et al. Chemical etch monitor for measuring film etching during a chemical etching process.
6. U.S. Pat. No. 5,573,623 (1996) Barbee, et al. Apparatus for contactless real-time in-situ monitoring of a chemical etching process
7. U.S. Pat. No. 5,516,399 (1996) Balconi-Lamica, et al. Contactless real time in situ monitoring of a chemical etching.
8. U.S. Pat. No. 5,450,205 (1995) Sawin, et al. Apparatus and method for real time measurement of thin film layer thickness and changes thereof.
9. U.S. Pat. No. 5,392,124 (1995) Barbee, et al. Method and apparatus for real-time in-situ endpoint detection and closed loop etch process control 10. U.S. Pat. No. 5,337,144 (1994) Strul, et al. Etch rate monitor using collimated light and method using same
12. U.S. Pat. No. 5,097,130 (1992) Koashi, et al. Quantitative determination method for processing semiconductors and apparatus thereof
13. U.S. Pat. No. 4,710,261 (1987) Dennis, Apparatus and method for maintaining a uniform etching solution
14. U.S. Pat. No. 4,454,001 (1984) Sternheim, et al. Interferometric method and apparatus for measuring etch rate and fabricating devices
15. U.S. Pat. No. 4,060,097 (1977) Oxford, Automatic etching system
16. U.S. Pat. No. 6,013,165 (2000) Holbrook et al. Bubble monitor for semiconductor manufacturing
17. U.S. Pat. No. 6,203,659 (2001) Shen, et al. Method and apparatus for controlling the quality of a photoresist stripper bath It will be understood by one skilled in the art that aspects of the present invention described hereinabove may be embodied in a computer running software, and that the software may be supplied and stored in tangible media, e.g., hard disks, floppy disks or compact disks, or in intangible media, e.g., in an electronic memory, or on a network such as the Internet.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for real-time dynamic analysis of chemical etching, comprising the steps of:
   passing electromagnetic radiation from an electromagnetic radiation source through an aqueous etchant solution comprising at least one inorganic etchant species, at at least two points in time, wherein said aqueous etchant solution is operative to etch an inorganic solid;
   performing ex situ non-contact scanning detection over a predetermined spectral range of said electromagnetic radiation passed through said aqueous etchant solution, by means of a detector over said at least at two points in time so as to detect at least one change in at least one optical property of said aqueous etchant solution over said predetermined spectral range; and
   comparing said at least one change in said at least one optical property over said predetermined spectral range at said at least two points in time by means of an algorithm in a processor so as to provide a rate of etching of said inorganic solid, wherein said algorithm includes a calibration model developed by using a method comprising the steps of:
      obtaining a plurality of calibration samples of the aqueous etchant solution, wherein each calibration sample has a known etch rate, and irradiating said plurality of calibration samples of the aqueous etchant solution with electromagnetic radiation and recording their respective at least one optical property over said predetermined spectral range;
      determining variations of their respective at least one optical property over said predetermined spectral range so as to correlate at least one optical property of said plurality of calibration samples with said known etch rate; and
      developing a calibration model based on the results of said step of determining.

2. A method according to claim 1, wherein said step of passing includes:
   i) emitting electromagnetic radiation in said predetermined spectral range from an electromagnetic radiation source, wherein said electromagnetic radiation is near infrared radiation in the spectral range of 700-1900 nm;
   ii) transmitting said near infrared electromagnetic radiation via a first optical transmission element from said near infrared electromagnetic radiation source through a sampling element containing a sample of said aqueous etchant solution comprising at least one inorganic etchant species and at least one byproduct species having etchant properties; and
   iii) conveying output near infrared electromagnetic radiation from said sample via a second optical transmission element to said detector.

3. A method according to claim 1, wherein said step of comparing further comprises a step of performing a chemometric manipulation on data relating to said at least one change in said at least one optical property over the predetermined spectral range.

4. A method according to claim 1, wherein said algorithm further provides a differential rate of change of said etching of said inorganic solid over a period of time.

5. A method according to claim 1, wherein said algorithm further provides a rate of etching of said inorganic solid and allows for regularly adjusting the etch rate of said aqueous etchant solution.

6. A method according to claim 1, wherein said aqueous etchant solution comprises ions selected from the group consisting of halide ions, sulfate ions, sulfite ions, nitrite ions, nitrate ions, chromate ions, persulfate ions, phosphate ions, and nitride ions.

7. A method according to claim 1, wherein said step of passing further comprises passing said aqueous etchant solution through a sampling element having a substantially transparent sampling tube.

8. A method according to claim 1, further comprising a step of detecting a fault in a rate of addition of a replenishing chemical component of said aqueous etchant solution.

9. A method according to claim 1, wherein said step of comparing further comprises detecting a bubble in said aqueous etchant solution.

10. A method according to claim 1, wherein said method is independent of a presence of bubbles in said aqueous etchant solution.

11. A method according to claim 1, wherein said method is independent of the temperature of said aqueous etchant solution.

12. A method according to claim 1, further comprising the steps of:
   applying computer software to data relating to said at least one change in said at least one optical property so as to provide an updated algorithm; and
   applying said updated algorithm to data relating to a new sample of said aqueous etchant solution so as to further provide a rate of etching of said inorganic solid in said new sample.

13. A method according to claim 1, wherein said inorganic solid is a solid containing silicon.

14. A method according to claim 13, wherein said solid containing silicon is selected from a group of solids consisting of Si, $SiO_2$, and SiN.

15. A method according to claim 1, wherein said model upon which said algorithm is based further takes into account effects of different solution circulation and flow rates.

16. A method according to claim 1, wherein said known etch rate is determined by thickness measurements.

17. A method according to claim 1, wherein said at least one optical property is spectral scanning transmission intensities.

* * * * *